(12) United States Patent
Forsvall

(10) Patent No.: US 11,701,474 B2
(45) Date of Patent: Jul. 18, 2023

(54) NEEDLE ARRANGEMENT

(71) Applicant: XAGA SURGICAL AB, Helsingborg (SE)

(72) Inventor: Andreas Forsvall, Helsingborg (SE)

(73) Assignee: SAGA SURGICAL AB

( * ) Notice: Subject to any disclaimer, the term of this patent is extended or adjusted under 35 U.S.C. 154(b) by 1075 days.

(21) Appl. No.: 16/324,548

(22) PCT Filed: Jan. 16, 2017

(86) PCT No.: PCT/EP2017/050804
§ 371 (c)(1),
(2) Date: Feb. 8, 2019

(87) PCT Pub. No.: WO2018/028837
PCT Pub. Date: Feb. 15, 2018

(65) Prior Publication Data
US 2019/0175842 A1    Jun. 13, 2019

(30) Foreign Application Priority Data

Aug. 10, 2016   (WO) ................. PCT/EP2016/069070

(51) Int. Cl.
*A61M 5/32*  (2006.01)
*A61B 10/00*  (2006.01)
(Continued)

(52) U.S. Cl.
CPC ....... *A61M 5/3202* (2013.01); *A61B 10/0048* (2013.01); *A61B 10/0241* (2013.01);
(Continued)

(58) Field of Classification Search
CPC .... A61M 5/3202; A61M 1/76; A61M 5/2033; A61M 5/3234; A61M 5/3286;
(Continued)

(56) References Cited

U.S. PATENT DOCUMENTS 6,050,955 A  4/2000 Bryan et al.
6,491,670 B1  12/2002 Toth et al.
(Continued)

FOREIGN PATENT DOCUMENTS

WO  02/062231  8/2002
WO  2007/074123  7/2007
(Continued)

OTHER PUBLICATIONS

Chinese First Office Action (CN Application No. 201780049419.8) dated Apr. 16, 2021, 13 pages, English Translation.
(Continued)

*Primary Examiner* — Patrick Fernandes
(74) *Attorney, Agent, or Firm* — Quarles & Brady LLP

(57) ABSTRACT

A medical needle arrangement (100, 1000, 1400) is disclosed. The needle arrangement (100, 1000, 1400) comprises: a needle sheath (104, 002, 1402), and a needle (202, 1102, 1406) comprising: an elongated portion and a sealing member (204, 1003, 1403) being arranged to a front end of the elongated portion. The needle arrangement is adapted to bet set in: a closed position, in which the sealing member (204, 1003, 1403) is arranged to abut at least a portion of a front end surface of the needle sheath (104, 1002, 1402) thereby restricting intrusion of foreign matter in an area between the needle sheath and the needle, and an open position, in which a gap (1204, 1506) is formed between the sealing member (204, 1003, 1403) and the front end surface of the needle sheath (104, 1002, 1402). Embodiments include needle arrangement for injection, for aspiration, and for biopsy purposes.

17 Claims, 8 Drawing Sheets

(51) Int. Cl.
  *A61B 10/02* (2006.01)
  *A61M 5/20* (2006.01)
  *A61M 1/00* (2006.01)
(52) U.S. Cl.
  CPC ...... *A61B 10/0275* (2013.01); *A61B 10/0283* (2013.01); *A61M 1/76* (2021.05); *A61M 5/2033* (2013.01); *A61M 5/329* (2013.01); *A61M 5/3234* (2013.01); *A61M 5/3286* (2013.01); *A61B 2010/0208* (2013.01)

(58) Field of Classification Search
  CPC ............ A61M 5/329; A61M 2205/195; A61B 10/0048; A61B 10/0241; A61B 10/0275; A61B 10/0283; A61B 2010/0208; A61B 10/0233; A61B 2010/045
  See application file for complete search history.

(56) References Cited

U.S. PATENT DOCUMENTS

| | | |
|---|---|---|
| 2006/0178646 A1 | 8/2006 | Harris et al. |
| 2006/0189891 A1 | 8/2006 | Waxman et al. |
| 2015/0238173 A1 | 8/2015 | Wegener et al. |
| 2016/0081585 A1 | 3/2016 | Halter |

FOREIGN PATENT DOCUMENTS

| | | |
|---|---|---|
| WO | WO 2007-074123 A1 | 7/2007 |
| WO | 2016/161062 | 10/2016 |

OTHER PUBLICATIONS

Indian First Examination Report (IN Application No. 201917006328) dated May 25, 2021, 5 pages, English Translation.
International Preliminary Report on Patentability for PCT/EP2017/050804, dated Nov. 2, 2018, 7 pages.
International Search Report for PCT/EP2017/050804, dated May 9, 2017, 3 pages.

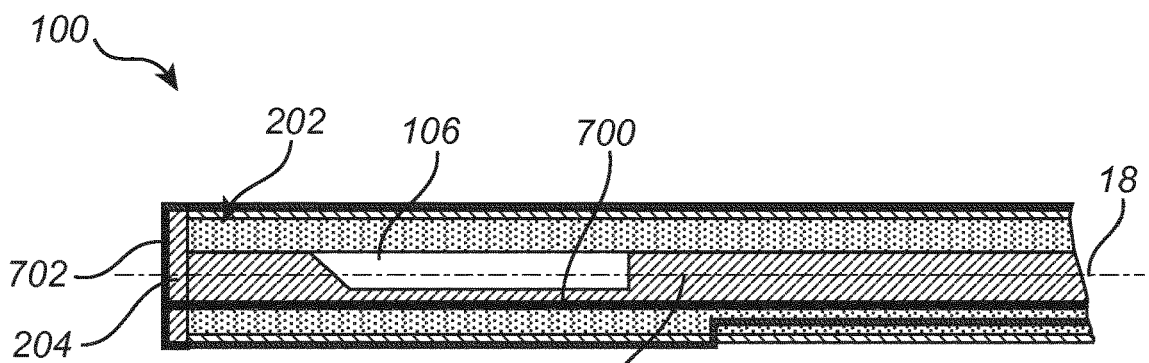
Fig. 7a
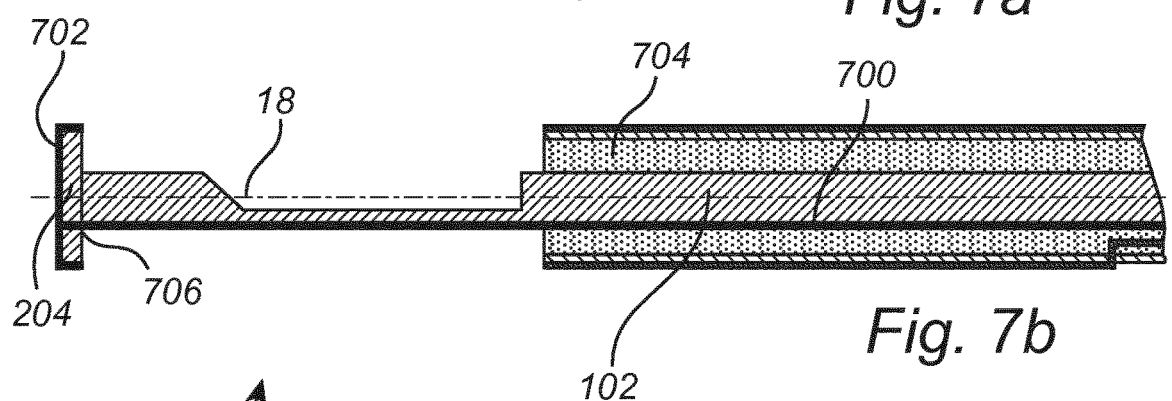
Fig. 7b
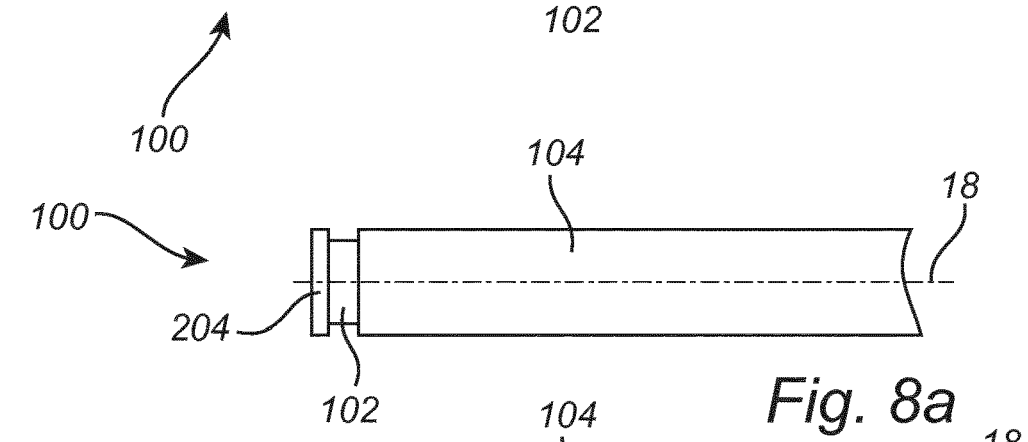
Fig. 8a
Fig. 8b
Fig. 8c

NEEDLE ARRANGEMENT

CROSS-REFERENCE TO RELATED APPLICATION

This application claims priority to and is a 35 U.S.C. § 371 national phase application of PCT/EP2017/050804 (WO2018/028837), filed on Jan. 16, 2017 entitled "A NEEDLE ARRANGEMENT", which application claims priority to and the benefit of PCT Patent Application No. PCT/EP2016/069070, filed Aug. 10, 2016, the disclosures of which are incorporated herein by reference in their entirety.

TECHNICAL FIELD

The invention relates to a needle arrangement for a medical application. Three different types of needle arrangements will be disclosed herein, namely a biopsy needle arrangement, an injection needle arrangement, and an aspiration needle arrangement.

BACKGROUND OF THE INVENTION

Within the field of medicine, needles for various purposes exist. For example, needle arrangements for injection, aspiration, and for taking biopsies are commonly used for different purposes. A common characteristic for these types of needle arrangements is that a needle of the needle arrangement is inserted into a body part (of a human) for performing, for example, an injection, an aspiration, or for collecting a biopsy sample. In connection with these types of invasive procedures there is always a risk of infection.

For example, when performing a trans rectal prostate biopsy (TRPB, which is the gold standard for diagnosis of prostate cancer, a biopsy needle is forwarded through the rectal wall and into the prostate. Normally, 8-12 biopsies are taken during the examination. A drawback with this method is a risk of infection due to intrusion of bacteria in the prostate during the medical procedure. In order to prevent infection antibiotics is often given by routine. With raising prevalence of multi-resistant bacteria, the number of infections risk to increase. Current studies show a sepsis rate of 1-5% after prostate biopsies. Another 5% suffers a milder infection treatable with per oral antibiotics (Lundström et al J Urol. 2014 October; 192 (4):1116-22).

Patients suffering sepsis after prostate biopsies normally require at least 2-3 days stay at the hospital receiving intravenous antibiotics. Some patients suffer long lasting troublesome infections and some lifelong morbidity. In an American study, the cost of sepsis was 5 900 US dollar per patient. In the US about 1 million biopsies are performed each year and approximately 3 million biopsies are performed yearly worldwide. 1.1 million persons are diagnosed with prostate cancer every year.

Lots of work has been made to prevent infections with for example rectal swabs and different antibiotics. However, there is still a need for improvements of needle arrangements, for example for application in the fields of biopsy sampling, such as prostate biopsy sampling, and in injection/aspiration applications, such as for amniocentesis and punctures.

SUMMARY OF THE INVENTION

In view of the above, it is an object of the present invention to provide a needle arrangement that provides a decreased risk of infections for the patient. Another object of the present invention is to lower the risk of infections due to an invasive procedure by a needle arrangement and to lower the general need for antibiotics, both in the precautionary and the treatment regimes. The needle arrangement, with different configurations that will be disclosed herein, is called a Forsvall needle and is configured with a Forsvall tip comprising a sealing member.

These and other objects of the inventive concept are at least partly met by the inventive concept as defined in the independent claim. Preferred embodiments are set out in the dependent claims.

According to a first aspect of the invention, a needle arrangement for a medical application is provided. The needle arrangement comprises:

an elongated needle sheath having a front end and a rear end, and a needle comprising:

an elongated portion adapted to be coaxially arranged inside the needle sheath, and a sealing member being arranged to a front end of the elongated portion.

The needle arrangement is adapted to bet set in:

a closed position, in which the sealing member is arranged to abut at least a portion of a front end surface of the needle sheath extending transverse the longitudinal axis of the needle thereby restricting intrusion of foreign matter in an area between the needle sheath and the needle, and an open position, in which a longitudinal gap, extending in the longitudinal axis of the needle, is formed between the sealing member and the front end surface of the needle sheath.

In the context of this application, the following definitions apply.

The term coaxially arranged should be construed as sharing a common axis. The elongated portion is positioned inside the needle sheath and shares a common axis therewith. The common axis is referred to as the longitudinal axis.

The sealing member is arranged to abut at least a portion of the end surface of the needle sheath. Optimally, a perfect fit is achieved between the sealing member and the end surface. In reality, however, an interstice (i.e. a small gap) between the sealing member and the end surface may be present due to for example surface roughness or precision in fitting and/or manufacturing of the sealing member and/or the needle sheath. It should be noted that other structures, such as a coating, may be provided in the interface between the sealing member and the end surface, in which case the two parts are still defined as being abutting.

A gap may be present between the elongated portion of the needle and the needle sheath. Thus, there is a small distance between the needle and the needle sheath which provides an area referred to as a gap.

The term biopsy is conventionally referred to as 'the act of taking a biopsy', as well as 'a biopsy' being the sample itself. To facilitate the reading of this application, a biopsy will be referred to the procedure and biopsy sample will be referred to as the (tissue) sample being collected/obtained from the body during the biopsy.

Throughout the application, the term bacteria is used as an example of foreign matter, which should be construed in a broad sense as unwanted matter in the context of biopsy sampling. Other non-limiting examples of foreign matter are viruses and protozoa.

Details of the first aspect will now be disclosed.

A biopsy, injection, or aspiration process may comprise the step of entering multiple parts of the body with the needle arrangement, for example the biopsy needle arrangement, and thereby there is a risk that the needle arrangement, for example the biopsy needle arrangement, transports bacteria between different parts. A risk of infection is thus present when performing biopsies.

For example, a biopsy of the type TRPB involves a step of entering the rectum of the patient and with a biopsy needle arrangement pierce the wall of the rectum. With it, the biopsy needle arrangement may carry bacteria, in for example grooves/holes on the outer surface structure thereof or in gaps between structures of the arrangement, from the rectum into the space between the rectum and the prostate and further into the prostate. The bacteria may, if brought into the prostate, cause a very severe and potentially life threatening infection in the body. A conventional needle arrangement, such as a conventional biopsy needle arrangement, may have a gap between a needle and a needle sheath. The entrance of the gap typically faces forward in the direction of travel when the biopsy needle arrangement is inserted in the body. By that the gap is open towards the direction of travel in such a way it is particularly prone to collect and bring along bacteria. Bacteria may also be collected by the outer surface structure of the needle arrangement, for example the biopsy needle arrangement, which typically is made of stainless steel.

By that the sealing member, comprised in the inventive needle arrangement, for example a biopsy needle arrangement, is connected to the needle and is arranged to abut at least a portion of the end surface of the needle sheath, the sealing member is arranged to cover at least a part of the entrance to the gap provided between the elongated portion of the needle and the needle sheath. By covering the entrance facing the forward movement direction of the biopsy needle arrangement, the risk of collecting and bringing with bacteria is reduced. It is noted that a gap between the sealing member and the end surface of the needle sheath may be provided, however an entrance to such a gap is now directed in a direction being transversal to the longitudinal direction, i.e. transversal to the direction of movement, thereby contributing to a reduced risk of collecting bacteria. Moreover, a strong fit between the sealing member and the needle sheath may be achieved by forcing the sealing member and the needle sheath towards each other (by for example a spring mechanism) which contributes to a minimized interstice between the parts. The gap between the needle and the needle sheath cannot be minimized in such manner since that would create a frictional force between the parts which would counteract movement of the needle in relation to the needle sheath and thus the function of the needle arrangement, for example the biopsy needle arrangement. Hence, the risk of that bacteria is collected in the interstice between the sealing member and the needle sheath is reduced by the above mentioned factors, i.e. the repositioned entrance and the strong fit, when compared to the risk of collecting bacteria in a conventional needle arrangement, for example a conventional biopsy needle arrangement.

When the needle is arranged in the closed position, also referred to as a retracted portion, the sealing member abuts at least a portion of the end of the needle sheath. Notwithstanding the fact that there may always be an interstice between the two parts, as soon as the sealing member no longer abuts the end surface of the end of the needle sheath, the needle may be considered to be in the open position, also referred to as an extraction position.

Applications for the needle arrangement according to the invention include, for example, biopsy sampling, amniocentesis and punctures of various kinds.

A connection member may be arranged to the rear end of the needle sheath and adapted to connect to an actuator or to a syringe.

The actuator may be provided for actuating the needle out from the needle sheath. The actuator may be part of a system that comprises the needle arrangement provided for biopsy purposes, and further comprising arrangements for actuating retraction/extraction movements in the biopsy needle arrangement, tubes, and holders.

The syringe may be utilized in applications where the needle arrangement is used for injection or aspiration. The connection member may have various configurations depending on the actuator or syringe that it is adapted to connect to. Non-limiting examples of different configurations will be provided in the detailed description.

The connection member may comprise a biasing means arranged to bias the needle arrangement to be set in the closed position. The biasing means may comprise a spring mechanism. It is advantageous to have the needle arrangement set and maintained in the closed position when the needle is not in an active mode, i.e. when it is not set in the open position for sampling (when taking a biopsy), for injection, or for aspiration.

A needle arrangement adapted for an injection application or for an aspiration application may be configured such that a channel is provided between the front end and the rear end of the needle sheath. The cannel may extend along the longitudinal axis of the needle. The channel may be provided between the needle sheath and the needle or inside the needle. The connection member may be adapted to connect the needle arrangement to a syringe such that a fluid communication is allowed between the syringe and the longitudinal gap being formed when the needle arrangement is set in the open position.

In one embodiment of the needle arrangement adapted for an injection application, the connection member is arranged to connect to a tip of the syringe. The channel may be provided between the needle sheath and the needle. In a needle arrangement for an injection application, it is advantageous that the channel of the needle arrangement is provided between the needle and the needle sheath. In such a configuration, a flow of liquid may be present between the sealing member and a front end surface of the needle sheath.

Further, the biasing means may comprise a spring member that extends in parallel to the longitudinal axis of the needle and between the connection member and a part of the needle. The spring member may be arranged to be compressed when exerted to a liquid pressure during injection of a liquid by a thereto connected syringe, whereby the needle arrangement is set in the open position. In one embodiment, the spring member comprises a spring element that extends between an inner wall portion of the connection member and an end plate arranged to a back portion of the needle. Such a configuration may contribute to a compact needle arrangement.

A guiding mechanism may be provided. The purpose of the guiding mechanism is to guide the sealing member towards an aligned position relative the needle sheath while the needle arrangement is set towards the closed position. By aligned position is meant a predetermined relative position between the sealing member and the needle sheath that is desired for an application.

In one embodiment, the guiding mechanism may be provided by one or more guiding portion(s) of the needle. The one or more guiding portions are arranged to a front portion of the elongated portion for guiding the sealing member towards an aligned position relative the needle sheath while the needle arrangement is set from the open position to the closed position.

In one embodiment, the guiding portion comprises a plurality of flanges extending between the elongated portion of the needle and the needle sheath.

In one embodiment, the guiding portion comprises a conical portion formed around the longitudinal axis of the needle and being oriented with its base facing the sealing member.

In one embodiment, the guiding mechanism may be provided by the configuration of an interface between the sealing member and the needle sheath.

In one embodiment of the needle arrangement adapted for an aspiration application, the channel is provided inside the needle. Further, a rear end of the needle may be arranged to connect to a tip of the syringe. The connection member may comprise a syringe housing adapted to receive at least a part of a barrel of the syringe. The needle may be arranged to, when connected to the tip of the syringe, be forced forward along the longitudinal axis while the syringe is inserted to be received in the syringe housing, thereby setting the needle arrangement in the open position.

In one embodiment, the biasing means comprises a spring member, such as a helical spring element, extending in parallel with the longitudinal axis of the needle and between the connection member and a front portion of the barrel of the syringe when received in the syringe housing. An advantage with this configuration is that a user does not need to manually retract the needle into the needle sheath for ensuring a sealing between the sealing member and the needle sheath.

In one embodiment, the connection member comprises a locking mechanism, for example in the form of a locking element, for locking the barrel of the syringe when received in the syringe housing for lockingly setting of the needle arrangement in the open position. An advantage by this configuration is that a user does not need to actively hold the syringe in the inserted position. This freedom provides for a less complex aspiration process.

In one embodiment of the needle arrangement adapted for a biopsy application, a compartment may be provided in the elongated portion of the needle such that the compartment is exposed to a surrounding area when the needle arrangement is set in the open position.

Different embodiments which may be applied to a needle arrangement according to the invention, for example an injection needle arrangement, an aspiration needle arrangement, or a biopsy needle arrangement, will now be disclosed.

In one embodiment of the needle arrangement, the sealing member is arranged to abut the complete end surface of the needle sheath when the needle is arranged in the retraction position. The sealing member may be arranged to have the same cross-sectional shape and size as the needle sheath, so as to provide a smooth transition between the outer surfaces of the sealing member and the needle sheath when the needle is arranged in the retraction position. Such a smooth transition may contribute to a reduced risk of collecting bacteria in the biopsy needle arrangement.

In one embodiment of the needle arrangement, the distal outer surface of the sealing member is inclined relative to the longitudinal axis of the needle. As the needle arrangement, for example the biopsy needle arrangement, moves in the forward movement direction, being essentially the same as the longitudinal direction, the shape of the sealing member may be chosen to facilitate the movement. By having the distal outer surface shaped in an inclination relative the longitudinal axis of the needle, and hence relative the movement direction of the biopsy needle arrangement, a pointy tip may be provided that is facing in the forward movement direction. The needle arrangement, for example the biopsy needle arrangement, may thereby move more easily through the tissue and pierce, for example, the wall of the rectum easier.

In a preferred embodiment, the inclination angle between the distal outer surface and the longitudinal axis of the needle is in the interval of 30-60 degrees. A pointy tip obtained by an inclination with an inclination angle in this interval may facilitate the movement of the needle arrangement, for example the biopsy needle arrangement, through tissue.

In an embodiment of the needle arrangement, the end surface of the needle sheath is inclined relative to the longitudinal axis of the needle. The sealing member surface abutting at least a portion of the end surface of the needle sheath is in such an embodiment inclined in a corresponding manner. In other words, the inner surface of the sealing member and the end surface of the needle sheath are inclined relative to the longitudinal axis by the same inclination angle.

In another embodiment of the needle arrangement, the end surface of the needle sheath is arranged orthogonally to the longitudinal axis of the needle. The sealing member surface abutting at least a portion of the end surface of the needle sheath is in such an embodiment also arranged orthogonally. Such a configuration of the needle sheath arrangement allows for the needle to rotate in relation to the needle sheath. Such control and maneuverability of the needle in relation to the needle sheath may be desirable in some applications. Moreover, the interface area between the sealing member and the needle sheath is minimized thus minimizing the area in which bacteria may be collected and/or tissue may be clamped when the needle goes from being in an extraction position to a retraction position.

In one embodiment of the needle arrangement, a coating, such as a repellent coating or a smooth nanocoating, is provided on at least a distal outer surface of the sealing member.

The smooth nanocoating provides a smooth surface, having a low surface roughness, in which bacteria is less prone to be collected when compared to material used for conventional needle arrangement, for example conventional biopsy needle arrangements, such as stainless steel. The smooth nanocoating may provide an especially even surface, with a very low amount of microscopic grooves and holes.

The repellent coating may comprise a material that has a low affinity for the foreign matter. By, for example, having a material that repels proteins, a lower number of binding sites are presented to the binding protein structures of the bacteria. It should be noted that there are many ways for the skilled person to chemically alter the surface to prevent foreign matter from adhering.

In one embodiment of the needle arrangement, a heat coating is provided on at least a distal outer surface of the sealing member. By heat coating is meant a coating which may be heated up by providing a current through the heat coating or by radiation provided by an external energy source. The heat coating may for example be activated to produce heat by providing a current through the heat coating which in that case has a relatively high resistance. As another example, the heat coating may be heated by subjecting it to radiation from an external energy source, such as a laser source.

By heating sections of the needle arrangement, for example the biopsy needle arrangement, that is exposed to bacteria, the bacteria will be thermally eliminated. Eliminating or at least reducing the amount of bacteria on and/or in the needle arrangement, for example the biopsy needle arrangement, may lower or eliminate the risk of infections.

In one embodiment of the needle arrangement, where the heat coating is arranged to develop heat when a current is applied there through, the heat coating may be a heat nanocoating. When using such resistive heating, the voltage drop depends on, among other things, the thickness of the material. By using a heat nanocoating, heating occurs quickly. Such a feature may be an advantage when heat is desired at a precise moment. A heat nanocoating also ensures quick cooling, which contributes to a minimized time of exposing surrounding tissue for potentially damaging heat.

In one embodiment of the needle arrangement, the heat coating is provided in an interface between the sealing member and the needle sheath. Preferably, the heat coating is provided in the whole interface, i.e. in the whole gap between the sealing member and the needle sheath. Bacteria which may have been collected in this area may thereby be heated and thus eliminated or at least reduced in number.

In one embodiment of the needle arrangement, the heat coating is provided along an outer surface portion of the needle sheath. The heat coating may be arranged in connection to the distal end thereof. As bacteria may also be collected on and/or by the outer surface of the needle sheath, this section may advantageously be coated with heat coating. Preferably, the whole outer surface of the biopsy needle arrangement that enters an area that is sensitive for contamination, such as a prostate in TRPB, may be coated with the heat coating.

In one embodiment of the needle arrangement, the needle arrangement, for example the biopsy needle arrangement, comprises an electrically conductive section connected to the heat coating and arranged to provide a conductive path through the needle arrangement, for example the biopsy needle arrangement. The conductive section inside the needle arrangement, for example the biopsy needle arrangement, is arranged to provide current through a heat coating, preferably a heat nanocoating that is arranged to produce heat when subjected to a current.

In one embodiment, the electrically conductive section comprises one or several of the following materials: carbon fiber, metals, such as gold and silver.

In one embodiment, the smooth nanocoating, the repellent coating and/or the heat nanocoating comprises one or several of the following materials: metals, carbon and carbon fibers, polyethylene glycol, PEG, (L-lysine)-[g]-poly(ethylene glycol), PLL-PEG or oxides such as titanium dioxide, silicon dioxide, and niobium petoxide.

It is noted that a particular nanocoating, or other material, may fulfil the characteristics of a combination of one or more of a smooth nanocoating and a heat nanocoating. In other words, the needle arrangement, for example the biopsy needle arrangement, may be provided with a single coating that provides the function of both a smooth nanocoating and a heat nanocoating.

In one embodiment, the complete outer surface of a distal portion of the needle arrangement, for example the biopsy needle arrangement, is provided with a coating, for example a smooth nanocoating, a repellent coating, a heat coating, or a combination thereof, wherein the distal portion corresponds to the portion that is to be inserted in a region of the body, for example a biopsy region. By biopsy region is meant for example the organ that the biopsy is to be sampled from. For a prostate biopsy, the biopsy region is the prostate region.

In one embodiment, the biopsy needle arrangement is configured for prostate biopsy.

In summary, the sealing member of the needle arrangement, for example the biopsy needle arrangement, contributes to lowering the number of bacteria that is collected and brought with the needle arrangement, for example the biopsy needle arrangement, from for example an area in the rectum, through the wall of the rectum and into the prostate. Surface treatment, such as coatings, and/or heat elements may be applied to an outer surface (portion) of the needle arrangement, for example the biopsy needle arrangement to (further) lower the risk that bacteria is collected.

The needle arrangement, or parts thereof, may be provided as a disposable article or as a non-disposable article.

A further scope of applicability of the present invention will become apparent from the detailed description given below. It is to be understood that this invention is not limited to the particular component parts of the arrangements and systems described as such arrangements and systems vary. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

BRIEF DESCRIPTION OF DRAWINGS

The above and other aspects of the present invention will now be described in more detail, with reference to appended drawings showing embodiments of the invention. The figures should not be considered limiting the invention to the specific embodiment; instead they are used for explaining and understanding the invention.

As illustrated in the figures, the sizes of layers and regions, such as gaps between structures, are exaggerated for illustrative purposes and, thus, are provided to illustrate the general structures of embodiments of the present invention. Like reference numerals refer to like elements throughout.

FIGS. 7a-b are cross-sectional views taken along the longitudinal axis of a biopsy needle arrangement, wherein the needle comprises a conductive section.

FIGS. 8a-c are cross-sectional views taken along the longitudinal axis of a biopsy needle arrangement showing shapes of the sealing member according to different embodiments.

Note that figures are not to scale for purposes of clarity.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and to fully convey the scope of the invention to the skilled person.

Embodiments of the present invention relate, in general, to the field of prostate biopsy, to injection applications, and to aspiration applications.

Preferred embodiments which will be disclosed relate to a biopsy needle arrangement, to an injection needle arrangement, and to an aspiration needle arrangement.

First, an embodiment relating to a biopsy needle arrangement will be described with reference to FIGS. 1-5c.

A preferred embodiment relates to the biopsy of the prostate, however, it should be appreciated that the invention is as such equally applicable to performing biopsy on other organs or parts of the male, female and/or an animal body. However, for the sake of clarity and simplicity, most embodiments outlined in this specification are related to prostate biopsy only.

Figure 1:
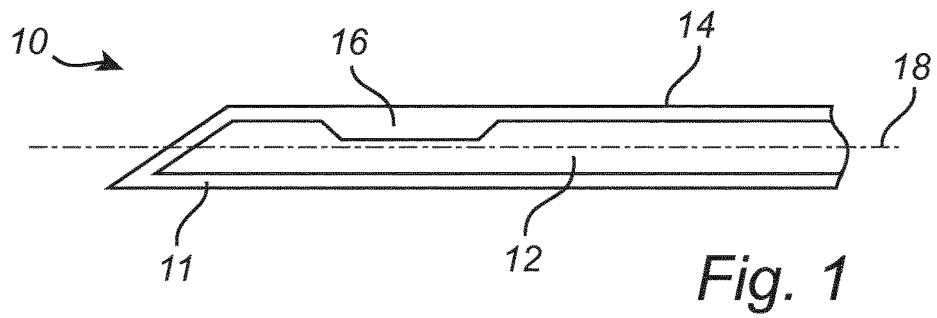
FIG. 1 is a schematic view of a conventional biopsy needle arrangement.

FIG. 1 is a schematic view of a conventional, so called tru-cut biopsy needle arrangement 10. The biopsy needle arrangement 10 may be part of a system for performing biopsy of any type, including prostate biopsies. The system may further comprise arrangements for actuating retraction/extraction movements in the biopsy needle arrangement, tubes, and holders.

The biopsy needle arrangement 10 comprises a needle 12 which is arranged inside a needle sheath 14. The biopsy needle arrangement 10 further comprises a compartment 16, for housing a biopsy sample (not illustrated). The needle 12 is movable relative to the needle sheath 14 along the longitudinal axis 18 of the biopsy needle arrangement 10. The biopsy needle arrangement 10 is arranged to be moved in the longitudinal direction, i.e. along the longitudinal axis 18. In order to facilitate movement of the biopsy needle arrangement 10 through tissue when the biopsy needle arrangement 10 is inserted into the body, the distal end of the needle sheath 14 and the elongated portion 12 may be inclined relative to the longitudinal axis 18.

The needle 12 and the elongated needle sheath 14 may be connected to springs for actuating movement of the needle 12 and the needle sheath 14 in relation to each other. The movement of the needle 12 and the needle sheath 14 may be independently controlled.

When performing, for example, a TRPB, an ultrasound device is inserted into the rectum of the patient in order to visualize the prostate and provide guidance through a canal for the biopsy needle arrangement 10. The biopsy needle arrangement 10 is then pierced through the wall of the rectum and into the prostate. The biopsy needle arrangement 10 normally penetrates the prostate by up to 6 cm.

The needle sheath 14 and the needle 12 may be arranged to be actuated in a forward directed movement in two steps. Firstly, the needle 12 is actuated out from the needle sheath 14 to an extraction position, exposing the compartment 16. Surrounding tissue is collected inside the exposed compartment 16. Closely after, normally within milliseconds, the needle sheath 14 is actuated forward thereby making the needle 12 revert to a retraction position. The compartment 16 now contains the collected biopsy sample. The biopsy needle arrangement 10 may then be pulled out of the prostate and the biopsy sample may be obtained from the compartment 16. Normally around 8-12 samples are extracted during one examination, however anything from 1 to more than 20 biopsies can be obtained.

The gap 11 between the needle sheath 14 and the needle 12 is exposed to the surroundings by a gap entrance which faces in the direction of travel. Bacteria are prone to be collected in the gap, especially during the travel in a forward direction through tissue while passing for example faeces with bacteria lining the inside of the rectal wall. The conventional biopsy needle arrangement 10 may thus collect and bring bacteria along with it when traveling through tissue which may increase the risk of post-examination infections.

The conventional biopsy needle arrangement 10 is typical made in stainless steel. Due to the surface roughness of such materials, bacteria may be collected and brought with the biopsy needle arrangement 10 on the outer surface of the needle sheath 14 and of the needle 12, respectively.

Figure 2:
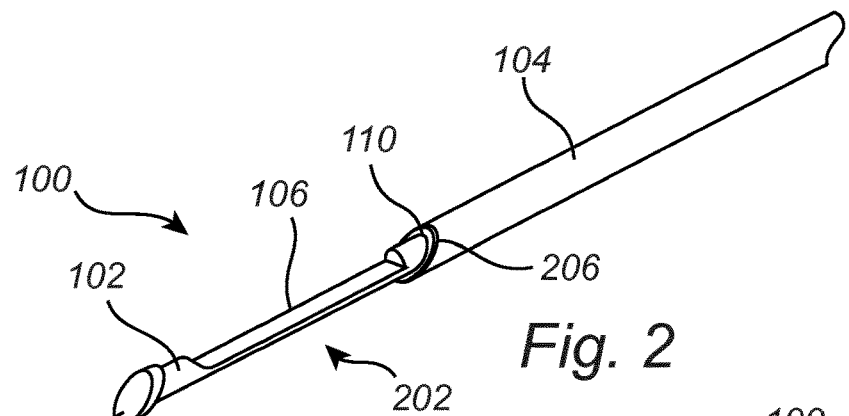
FIG. 2 is a perspective view of a biopsy needle arrangement according to an embodiment.

FIG. 2 is a perspective view of a needle arrangement 100 according to an embodiment relating to a biopsy needle arrangement. The biopsy needle arrangement 100 comprises a needle 202 and an elongated needle sheath 104. The biopsy needle arrangement 100 may typically be 20 or 25 cm long. The biopsy needle arrangement, or any needle arrangement according to an embodiment, may of course be of any length suitable the application. The length and dimensions of the biopsy needle arrangements and its components (needle/needle sheath thickness, compartment dimension, etc.) may vary between different applications.

The needle 202 comprises an elongated portion 102 and a sealing member 204. The elongated portion 102 forms a compartment 106 for housing a collected tissue sample (not illustrated). The compartment 106 may be 1-3 cm long. In a preferred embodiment, the compartment 106 is situated close to the sealing member 204, such as at a distance of 1-7 mm.

The sealing member 204 may be an integral part of the elongated portion 102. The sealing member 204 may alternatively be attached to the elongated portion 102 using, for example, screwing, welding or gluing.

The biopsy needle arrangement 100 is shown with the needle 202 being in an extraction position, i.e. the needle arrangement 100 is set an open position.

The needle 202 may be arranged in a retraction position, i.e. in a closed position, by that the needle sheath 104 is forwarded to encompass the elongated portion 102 of the needle 202, wherein the sealing member 204 of the needle 202 abuts at least a portion of the end surface 206 of the needle sheath 104.

The end surface 206 is the area of the needle sheath 104 that is facing forward in the longitudinal direction of the biopsy needle arrangement 100, and towards the sealing member 204. By forward is meant in the direction of travel that the biopsy needle arrangement 100 is intended to travel when entering a part of the body for taking a sample. By backwards is meant the opposite direction to forward, also along the longitudinal axis 18. In other words, when entering a part of the body for taking a biopsy sample, the biopsy needle arrangement 100 travels in a forward direction and when being retracted through the tissue the biopsy needle arrangement 100 travels in a backward direction. This definition of forward and backward directions is applicable to other embodiments of a needle arrangement exemplified herein as well.

By that the sealing member 204 and the end surface 206 abuts when the needle 202 is in the retraction position, a gap entrance 110 to a longitudinal gap between the needle sheath 104 and the elongated portion 102 of the needle 202 is at least partly blocked by the sealing member 204 so that intrusion of foreign matter is prevented, or at least restricted. The sealing member 204 in the shown embodiment is arranged to cover the whole gap entrance 110 around the elongated portion 102 of the needle 202, but it is understood that even closing a part of the gap entrance 110 may contribute to a lowered risk for collecting bacteria. For example, the sealing member 204 may be arranged to cover a quarter or half of the edge of the gap entrance 110.

The sealing member 204 may have a different cross-sectional shape than that of the elongated portion 102 and/or of the needle sheath 104.

The biopsy needle arrangement 100 is in FIG. 2 shown to have a circular cross-sectional geometry but various other geometrical forms are possible. Non-limiting examples include rectangular and oval cross-sectional shapes.

Figure 3:
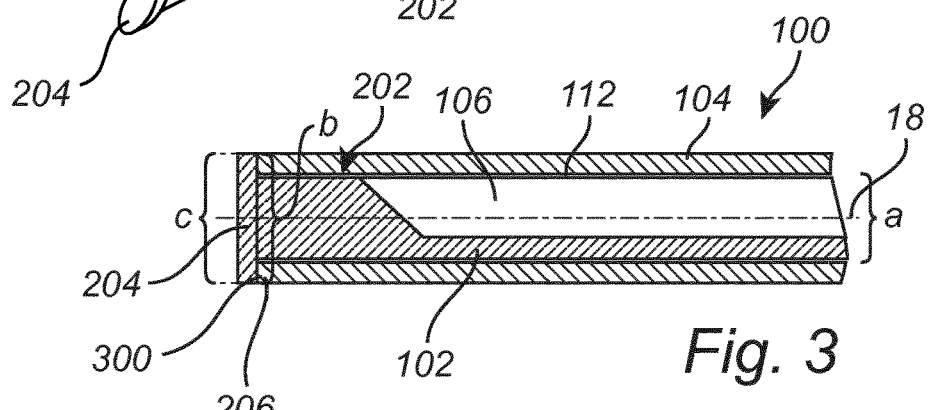
FIG. 3 is a cross-sectional view taken along the longitudinal axis of a biopsy needle arrangement according to an embodiment.

FIG. 3 illustrates a part of a biopsy needle arrangement 100 according to an embodiment. The biopsy needle arrangement 100 comprises a needle sheath 104 and a needle 202 coaxially arranged inside the needle sheath 104. The needle 202 is here arranged in a retraction position, i.e. the needle arrangement 100 is set in a closed position. A longitudinal gap 112 is present between the elongated portion 102 of the needle 202 to allow the needle 202, in particular the elongated portion 102 thereof, to easily move in relation to the needle sheath 104, i.e. without too much friction between the elongated portion 102 and the needle sheath 104. Optimally, the elongated portion 102 of the needle 202 is well fitted inside the needle sheath 104. In order to assist reading, however, the distances between the two parts are exaggerated in the figures.

Due to, for example, surface roughness, and/or lack of position preciseness or manufacturing precision, a transversal interstice 300 may be present between the sealing member 204 and the end surface 206 of needle sheath 104 when the sealing member 204 abuts the end surface 206. However, since the transversal interstice 300 is directed in a transversal direction, and thus the entrance of the transversal interstice 300 is not facing directly in the longitudinal direction, hence in the forward direction, as is the case of the entrance to the longitudinal gap 112 between the needle 102 and the needle sheath 104, the risk that bacteria is collected through the entrance of the transversal interstice 300 is lowered. Moreover, a strong fit between the sealing member 204 and the needle sheath 104 may be achieved by forcing the sealing member 204 and the needle sheath 104 towards each other which contributes to a minimized interstice 300 between the parts. The longitudinal gap 112 between the needle 102 and the needle sheath 104 cannot be minimized in such manner since that would create a frictional force between the parts which would counteract movement of the needle 104 in relation to the needle sheath 104 and thus the function of the biopsy needle arrangement 100. Hence, the risk of that bacteria is collected in the interstice 300 between the sealing member 204 and the needle sheath 104 is reduced by the above mentioned factors, i.e. the repositioned entrance of the interstice 300 and the strong fit between the sealing member 204 and the needle sheath 104, when compared to the risk of collecting bacteria in a conventional biopsy needle arrangement.

Additionally, a labyrinth effect is achieved since the transversal interstice 300 and the longitudinal gap 112 are not arranged in the same direction, further increasing the prevention of bacteria reaching the inside of the biopsy needle arrangement 100, in particular the compartment 106 provided therein.

The transversal interstice 300 may be minimized by a biasing means, such as a spring mechanism, arranged to actuate the needle sheath 104 forward towards the inner surface of the sealing member 204 such that the needle sheath 104 and the sealing member 204 are forced together. The biasing means may thus be arranged to bias the needle arrangement 100 to be set in the closed position. The biasing means, such as the spring mechanism, may be part of the biopsy needle arrangement 100.

In order to cover the gap entrance 110, the radial extension b of the sealing member 204 should be greater than the inner radial extension a of the needle sheath 104. In other words, in an embodiment where the cross-section of the sealing member 204 and of the needle sheath 104 is circular, the outer diameter of the sealing member 204 should be greater than the inner diameter 104 of the tubular needle sheath 104.

The radial extension b may be chosen such that the sealing member 204 completely covers the end surface 206 of the needle sheath 104. In FIG. 3, the radial extension b is equal to the outer radial extension c of the needle sheath 104. In this case, a smooth transition between the radial outer surface of the sealing member 204 and the radial outer surface of the needle sheath 104 is achieved. Such a smooth transition may contribute to a reduced risk of collecting bacteria in the biopsy needle arrangement 100, for example by reducing bacteria adhering to the end surface 206.

It is noted that the radial extension b of the sealing member 204 may in other embodiments be greater than the radial extension c of the needle sheath 104.

The sealing member 204 may be arranged to extend past the end surface 206 in the longitudinal direction and along the outer surface of the needle sheath 104. In such an embodiment, a second longitudinal gap will be present between the needle sheath 104 and the sealing member 204. An entrance to the second longitudinal gap will be facing away from the direction of forward movement of the biopsy needle arrangement 100 and thus there will still be a lowered risk of collecting bacteria through such an entrance when compared to conventional biopsy needle arrangements.

Figure 4A:
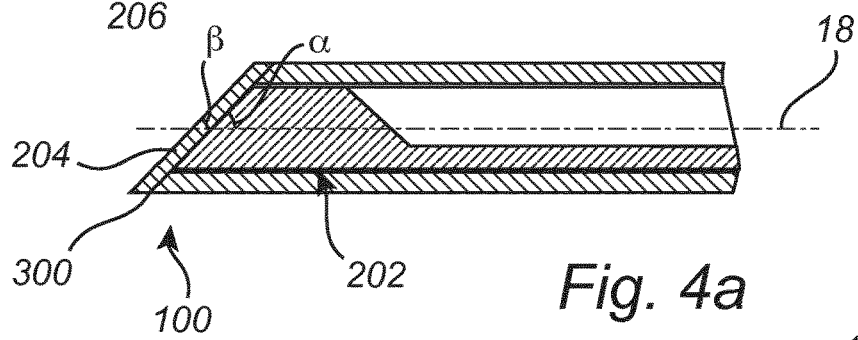
FIG. 4a is a cross-sectional view taken along the longitudinal axis of a biopsy needle arrangement, when the needle is in a retraction position.
Figure 4B:
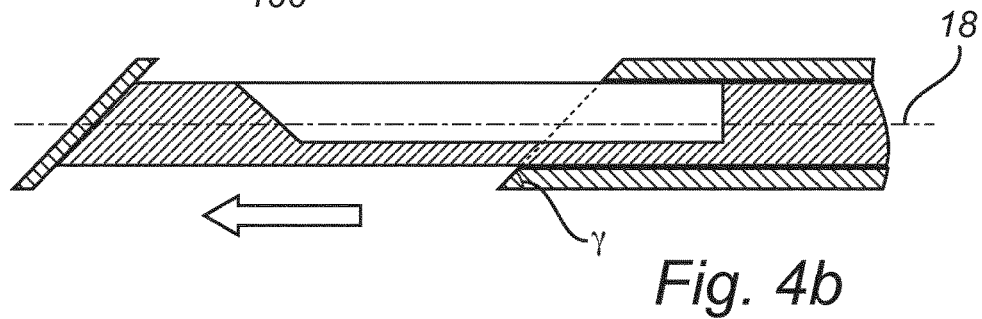
FIG. 4b is a cross-sectional view taken along the longitudinal axis of a biopsy needle arrangement, when the needle is in an extraction position.

FIGS. 4a and 4b are each a schematic view of the biopsy needle arrangement 100 according to an embodiment. The needle 202 is arranged in a retraction position.

The inner surface of the sealing member 204 may be inclined relative to the longitudinal axis 18. In a preferred embodiment, an inclination angle α is in the interval 30-60 degrees, relative to the longitudinal axis 18.

The inclination angle γ of the end surface 206 relative to the longitudinal axis 18 is equal to the inner surface inclination angle α of the sealing member 204.

The distal outer surface of the sealing member 204 is also inclined. The inclination angle β of the distal surface may differ from the inner surface inclination angle α. The distal surface inclination angle β is in the illustrated embodiment equal to the inner surface inclination angle α. Other distal surface inclination angles are possible, such as 0-90 degrees.

The inclination angles and shape of the sealing member 204 and the needle sheath 104 may affect the deviation angle and force needed to move the biopsy needle arrangement 100 through tissue.

FIG. 5 is a perspective view of a biopsy needle arrangement 100 according to an embodiment. A process of performing a TRPB biopsy with a biopsy needle arrangement 100 according to this embodiment will now be disclosed.

Figure 5A:
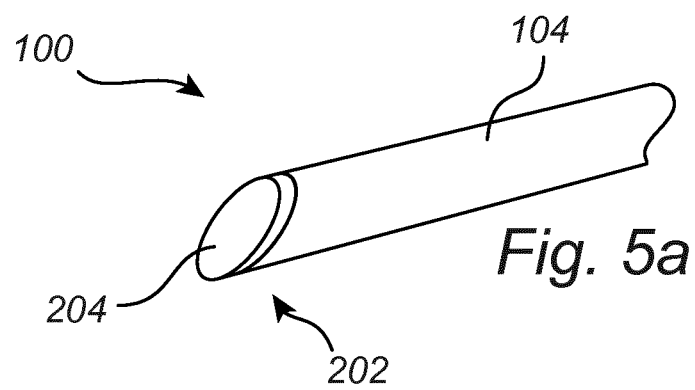
FIGS. 5a-c are perspective views of a biopsy needle arrangement in different configurations during a process of collecting a tissue sample.

FIG. 5a shows the biopsy needle arrangement 100 with the needle 202 arranged in a retraction position, i.e. the needle arrangement 100 is set in the closed position. The sealing member 204 effectively closes the gap 110 in accordance with above disclosed embodiments. The biopsy needle arrangement 100 may be inserted through a canal in the rectum of the patient, guided by an ultra sound device. The biopsy needle arrangement 100 is inserted by movement in a direction along the longitudinal direction of the biopsy needle arrangement 100 and with the sealing member 204 facing forward in the travel direction during insertion.

The biopsy needle arrangement 100 may be put against the rectum wall and aimed towards the prostate of the patient. The biopsy needle arrangement 100 may then be pushed through the wall and into the prostate. The biopsy needle arrangement 100 may be arranged to penetrate the prostate by up to 6 cm. The biopsy needle may also penetrate further into the prostate.

Figure 5B:
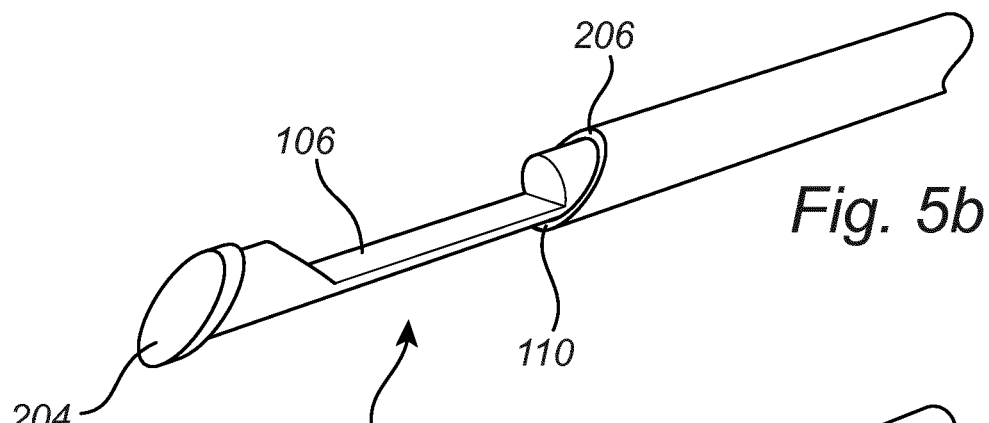

As illustrated in FIG. 5b, while in a desired position, the needle 202 may be actuated forward in relation to the needle sheath 104. The actuation may be achieved by a spring element or the like which may be part of the biopsy needle arrangement 100. The needle 202 may thus be moved further into the prostate. In this extraction position, i.e. when the needle arrangement 100 is set in this open position, the compartment 106 of the needle 202 is exposed by that a gap, extending in the longitudinal axis of the needle, is formed between the sealing member 204 and the end surface 206 of the needle sheath 104. A prostate biopsy sample may be collected in the compartment 106 of the needle 202.

Figure 5C:
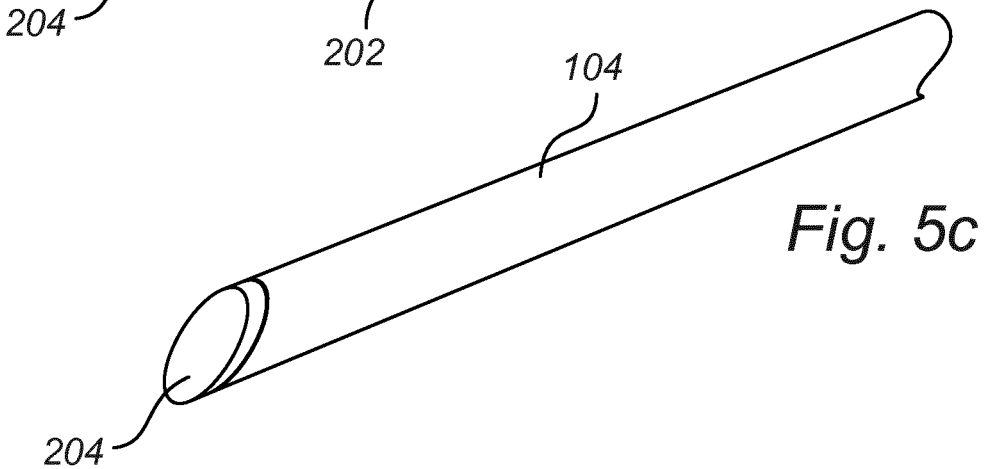

As illustrated in FIG. 5c, the needle sheath 104 may be actuated forward so as to encompass at least a part of the elongated portion 102 of the needle 202 and thus close the compartment 106. It may take a shorter or a longer amount of time for the needle sheath 104 to move forward.

The movement needle sheath 104, is restricted when impinging against the inner surface of the sealing member 204. In order to reduce possible damage of the sealing member 204, the biopsy needle arrangement 100, or a system that the biopsy needle arrangement 100 is part of, may be provided with a breaking mechanism so as to reduce the collision force.

The reader is reminded that the gap between the elongated portion 102 of the needle 202 and the needle sheath 104 is exaggerated for illustrative purposes.

Figure 6:
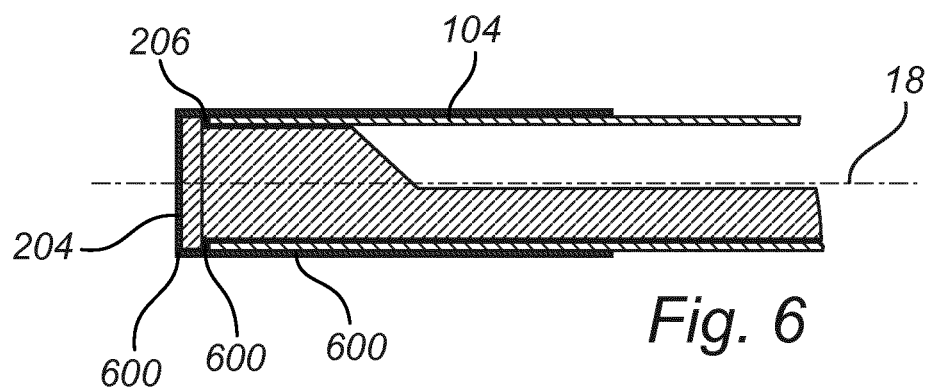
FIG. 6 is a cross-sectional view taken along the longitudinal axis of a biopsy needle arrangement being provided with a coating.

A schematic view of an embodiment of the biopsy needle arrangement 100 is illustrated in FIG. 6. Here, the needle 202 is arranged in a retraction position. That is, the needle arrangement 100 is set in a closed position.

When the biopsy needle arrangement 100 is moved from the rectum to the prostate, bacteria may get stuck in small grooves of the surface structure of the sealing member 204. This is the case with for example the material stainless steel which is conventionally used in this type of constructions.

In order to alleviate this effect, the sealing member 204 may partly, or completely, be coated in a coating 600. The coating 600 may be a repellent coating or a smooth nano-coating.

The term repellent is defined as surface structure that chemically lowers the adherence of bacteria when compared to conventionally used surface structures. For example, a surface structure that is hydrophobic lowers the adherence to the hydrophilic binding structures of bacteria. Non-limiting examples of the repellant coating are: metals, polymere brushes and/or zwitter ionic groups, such as PEG and PLL-PEG.

The term smooth is defined as an evenness of a surface structure, wherein the surface evenness contributes to that bacteria is less prone to adhere thereto when compared to conventionally used materials.

Non-limiting examples of the smooth nanocoating are: metals and Au.

The coating 600 may extend in the interface between the sealing member 204 and the needle sheath 104. This may be achieved by coating the end surface 206 of the needle sheath 104 and the inner surface of the sealing member 204 abutting the end surface 206 or provided on just one of the two. The interface between the inner surface of the sealing member 204 and the needle sheath 104 may take many different other forms in order to, for example, strengthen the labyrinth effect. For example, the inner surface of the sealing member 204 may form a conical recess in which the needle sheath 104, shaped in a corresponding manner, may be received.

The coating 600 may be provided on the outer surface of the needle sheath 104. The coating 600 may be provided on a part of the outer surface of the needle sheath 104, preferably at least the part that is inserted into the prostate. In a preferred embodiment, 6 cm of the needle sheath 104 as measured in the longitudinal direction and from the distal end is coated in coating 600. The distance 6 cm coincides with the distance of which the prostate is penetrated by the biopsy needle arrangement 100 in some applications.

In one embodiment, the coating 600 is provided along the whole outer surface of the needle sheath 104. This may be beneficial from a manufacturer perspective in that it may be less complex to coat the entire outer surface instead of a part thereof.

The application of coating 600 may be preceded by for example processing the material of the needle sheath 104 through, for example, electrochemical polishing. Another embodiment of the biopsy needle arrangement 100 is illustrated in FIG. 7a and FIG. 7b. The needle 202 illustrated in FIG. 7a is arranged in a retraction position.

A conductive section 700 is comprised in the biopsy needle arrangement 100. By conductive is meant electrically conductive in the context of this application.

The conductive section 700 runs inside the elongated portion 102 and forms an inner section of the elongated portion 102. The conductive section 700 may alternatively run along an outer surface of the elongated portion 102 of the needle 202.

The sealing member 204 is provided with a heat coating 702.

Non-limiting examples of the heat coating are: metals, carbon and carbon fibers. The conductive section 700 is conductively connected to the heat coating 702. The heat coating 702 may be a heat nanocoating. The heat nanocoating may also form a smooth nanocoating, and vice versa.

The heat coating 702 may also be arranged in the interface between the sealing member 204 and the needle sheath 104. This may be achieved by coating the end surface 206 of the needle sheath 104 and/or the inner surface of the sealing member 204 which is arranged to abut the end surface 206.

As illustrated, the heat coating 702 also extends on and along the outer surface of the needle sheath 104. The heat coating may be provided on parts of the needle sheath 104, preferably at least the part that is inserted into the prostate. In a preferred embodiment, 6 cm of the outer surface of the needle sheath 104 along the longitudinal extension and as measured from the distal end is covered by the heat coating 702. The distance 6 cm coincides with the distance of which the prostate is penetrated by the biopsy needle arrangement 100 in some applications.

In one embodiment, the heat coating 702 is provided along the whole outer surface of the needle sheath 104. This may be beneficial from a manufacturer perspective in that it may be less complex to coat the entire outer surface instead of a part thereof.

The heat coating 702 may be connected to a circuit (not illustrated) arranged in the biopsy needle arrangement 100 or in connection thereto. The heat coating 702 may be of a resistive material. By providing a current through the conductive section 700 of the biopsy needle arrangement 100, the current will flow also through the heat coating 702. By running a current through the heat coating 702, the material heats up. The heat coating 702 is preferably heated to at least 100 degrees Celsius, in order to eliminate any bacteria collected on the surface structure.

In one embodiment, the sealing member 204 comprises a connecting conductive section 706 arranged to conductively connect the conductive section 700 and the heat coating 702 of the sealing member 204.

The biopsy needle arrangement 100 may be constructed such that the current is disconnected when the needle 202 is arranged in the extraction position, as seen in FIG. 7b.

In a preferred embodiment, current is provided to the heat coating 702 of the sealing member 204 through the conductive section 700. The connecting section 706 bridges the connection between the conductive section 700 and the heat coating 702 of the sealing member 204. The skilled person appreciates that there may be other ways to connect the conductive section 700 with the heat coating 702 of the sealing member 204. For example, the sealing member may be of a conductive material, thereby in itself bridging the current from the conductive section 700 to the heat coating 702 of the sealing member 204.

Furthermore, the heat coating 702 of the needle sheath 104 provides a closed path for the current to return from the sealing member 204 back to a conductive return section (not shown in figures). It is appreciated that the conductive return section may be arranged differently in different configurations of the biopsy needle arrangement 100.

As can be seen in FIG. 7b, as soon as the needle 102 is arranged in an extracted position, the connection between the heat coating 702 of the needle sheath 104 and the heat coating 702 of the sealing member 204 may be disconnected. When the needle 102 is arranged in the extracted position, no current can flow through the biopsy needle 100.

In an embodiment, the conductive return section is connected to the power supply or to ground. In a preferred embodiment, the return section is placed inside the needle sheath 104, with a conductive bridge connecting the heat coating 702 with the return section through the need sheath 104 as is shown in FIG. 7a-b. The skilled person realizes that for the purpose of this embodiment, the return section may be placed on the outer surface of the needle sheath 104.

In order to reduce the risk that the biopsy sample becomes heat damaged, the sample is preferably kept below 41 degrees Celsius. For that purpose, part of the needle 202 may be made in an insulating material, thus forming an insulating portion 704. Specifically, the portion of the needle 202 forming the compartment 106 may be made in an insulating material. The insulating portion 704 may protect a biopsy sample in the compartment 106 from the heat developed in the heat coating 702. Insulating material may also be arranged as a part of the needle sheath 104. Specifically, an insulating material may be arranged in connection to the compartment 106 in order to protect a biopsy sample collected therein from heat. Non-limiting examples of insulating materials are: Kevlar, COP, PEEK and LCP.

In one preferred embodiment, the parts of the biopsy needle arrangement 100 not forming the disclosed conducting sections or the heat coating 702 are made of an insulating material.

In a preferred embodiment the heat coating 702 is formed by a nanocoating, being a thin coating. The term nanocoating is in the context of this application defined as a coating having a thickness of about 10-1000 nanometers. In the preferred embodiment, the thickness is about 100-400 nanometer. Such a thin heat coating 702 contributes to a quick heating and cooling process, with the effect of thermally eliminating bacteria on the surface of the heat coating with a lowered risk of damaging surrounding tissue.

It is appreciated that the concept of providing a coating 600 and the concept of providing a heat coating 702 may be applied to a needle arrangement according to any embodiment, not only a biopsy needle arrangement. Specifically, these coating concepts may be applied to an injection needle arrangement or to an aspiration needle arrangement according to embodiments. The skilled person may, by the above description of the coating concepts applied to a biopsy needle arrangement, translate the concepts to applications on other needle arrangements, such as an injection needle arrangement or an aspiration needle arrangement.

Different examples of configurations of the sealing member will now be disclosed with reference to FIGS. 8a-8c. These examples will be provided based on the above disclosed biopsy needle arrangement 100, however it is appreciated that configurations may be applied to other embodied needle arrangements as well, such as an injection needle arrangement or an aspiration needle arrangement.

As illustrated in FIGS. 8a-8c, the skilled person appreciates that the sealing member 204 may have many different shapes and forms. For example, the embodiment shown in FIG. 8b has an arrowhead configuration enabling better precision of the movement of the biopsy needle arrangement 100. Different shapes/forms of the sealing member 204 may be desired in different applications, for example between different biopsy techniques.

FIG. 8c illustrates a sealing member 204 with a distal outer surface angle that is inclined in an opposite direction relative to the inclination angle of the needle sheath 104. This configuration may provide a better precision, with low deviation, of the biopsy needle arrangement 100 when the needle 202 and the needle sheath 104, respectively, is actuated into the tissue.

Figure 9:
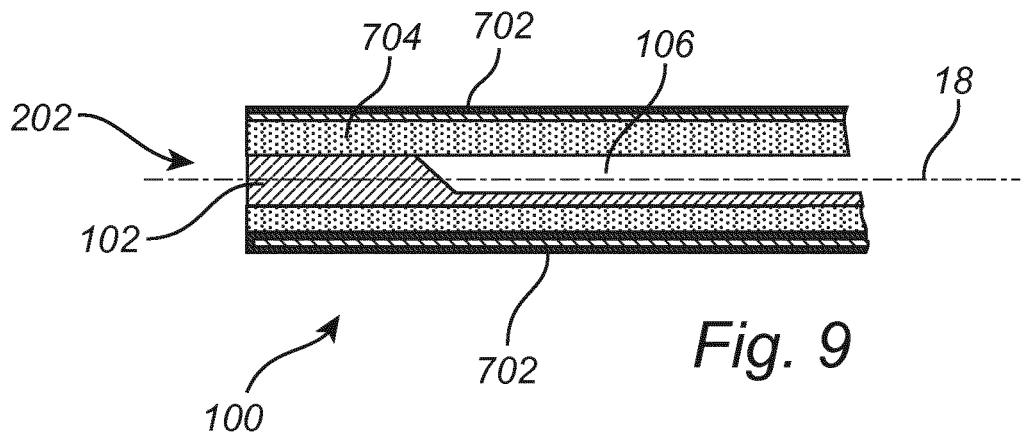
FIG. 9 is a cross-sectional view taken along the longitudinal axis of a biopsy needle arrangement according to an embodiment.

Another example of a biopsy needle arrangement 100 is illustrated in FIG. 9. The biopsy needle arrangement 100 comprises a needle 202 and a needle sheath 104. A heat coating 702 is provided with the corresponding form and function as disclosed above in connection to FIG. 7a and FIG. 7b. The heat coating 702 may be heated by providing a current through the heat coating 702. The current may be provided through a conductive portion 700 that is arranged to run inside or along the needle 202 and that is conductively connected to the heat coating 702. A conductive return section is also provided for providing a return path for the current, at least when the needle 202 is arranged in a retraction position.

An embodiment may be provided with a combination of the features of FIG. 7 and FIG. 9. In this embodiment, the current flowing through the needle sheath 104 is not disconnected while the needle 202 is in an extracted position. This concept is also applicable to other embodied needle arrangements such as an injection needle arrangement or an aspiration needle arrangement.

The conductive return section may be placed outside of the biopsy needle arrangement, for example it may comprise a conductive plate on the hip of the patient. In this case, the current is led through the conductive section 700, through the heat coating 702 and further through the tissue of the patient reaching the conductive plate, thereby completing the circuitry.

EXAMPLES OF CONFIGURATIONS OF A BIOPSY NEEDLE ARRANGEMENT

A1. A biopsy needle arrangement for obtaining a tissue sample, the biopsy needle arrangement comprising: an elongated needle sheath, a needle comprising an elongated portion coaxially arranged inside the needle sheath and movable between an extraction position and a retraction position in relation to the needle sheath, wherein the needle further comprises a sealing member arranged at a distal end of the elongated portion, the sealing member being arranged to abut at least a portion of an end surface of the needle sheath extending transverse the longitudinal axis of the needle when the needle is arranged in the retraction position, thereby restricting intrusion of foreign matter in an area between the needle sheath and the needle.

A2. The biopsy needle arrangement according to the example A1, wherein the sealing member is arranged to abut the complete end surface of the needle sheath when the needle is arranged in the retraction position.

A3. The biopsy needle arrangement according to any of the previous examples A1-A2, wherein a distal outer surface of the sealing member is inclined relative to the longitudinal axis of the needle.

A4. The biopsy needle arrangement according to example A3 wherein an inclination angle between the distal outer surface and the longitudinal axis of the needle is in the interval of 30-60 degrees.

A5. The biopsy needle arrangement according to any of the previous examples A1-A4, wherein the end surface of the needle sheath is inclined relative to the longitudinal axis of the needle.

A6. The biopsy needle arrangement according to any of the previous examples A1-A5, wherein the end surface of the needle sheath is arranged orthogonally to the longitudinal axis of the needle.

A7. The biopsy needle arrangement according to any of the previous examples A1-A6, wherein a coating, such as a smooth nanocoating or a repellent coating, is provided on at least a distal outer surface of the sealing member.

A8. The biopsy needle arrangement according to any one or the examples A1-A7, wherein a heat coating is provided on at least a distal outer surface of the sealing member.

A9. The biopsy needle arrangement according to the example A8, wherein the heat coating is a heat nanocoating.

A10. The biopsy needle arrangement according to any of the examples A8-A9, wherein the heat coating is provided in the interface between the sealing member and the needle sheath.

A11. The biopsy needle arrangement according to any of examples A8-A10, wherein the heat coating is provided along an outer surface portion of the needle sheath in connection to the distal end thereof.

A12. The biopsy needle arrangement according to any of the examples A8-A11, further comprising a conductive section connected to the heat coating and arranged to provide a conductive path through the biopsy needle arrangement.

A13. The biopsy needle arrangement according to the example A12, wherein the electrically conductive section comprises one or several of the following materials: carbon fiber, metals, such as gold and silver.

A14. The biopsy needle arrangement according to any of the previous examples A1-A13, wherein the arrangement is configured for prostate biopsy.

A15. A system comprising a biopsy needle arrangement according to any of the previous examples A1-A14.

Figure 10:
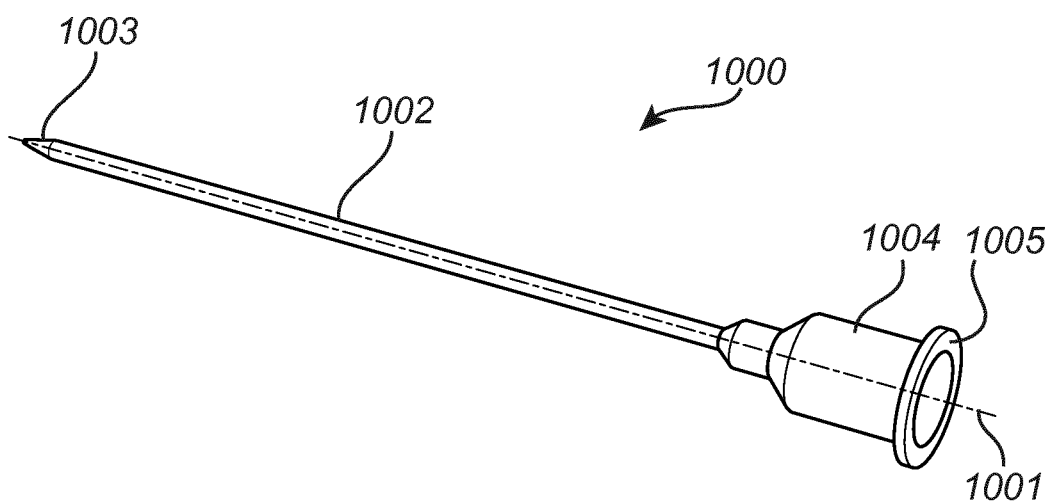
FIG. 10 illustrates a needle arrangement according to an embodiment of the invention.
Figure 11:
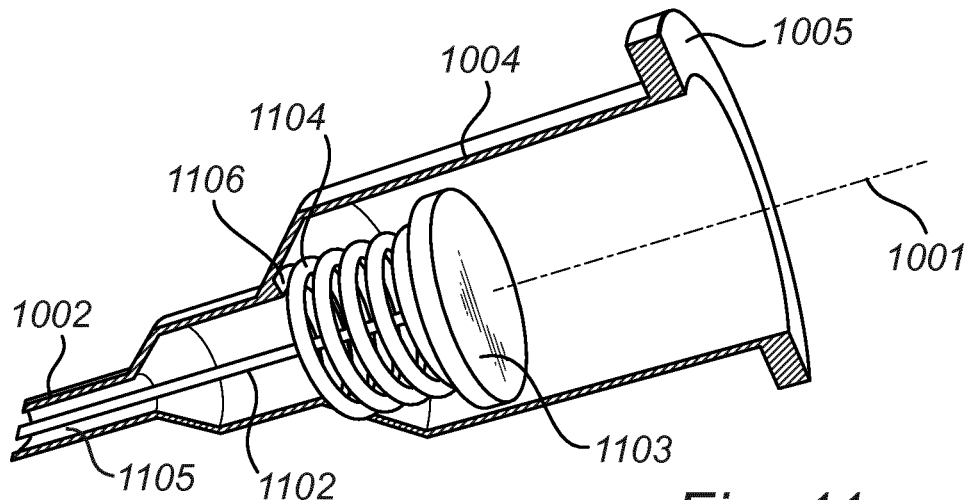
FIG. 11 illustrates a connection member of a needle arrangement.
Figure 12:
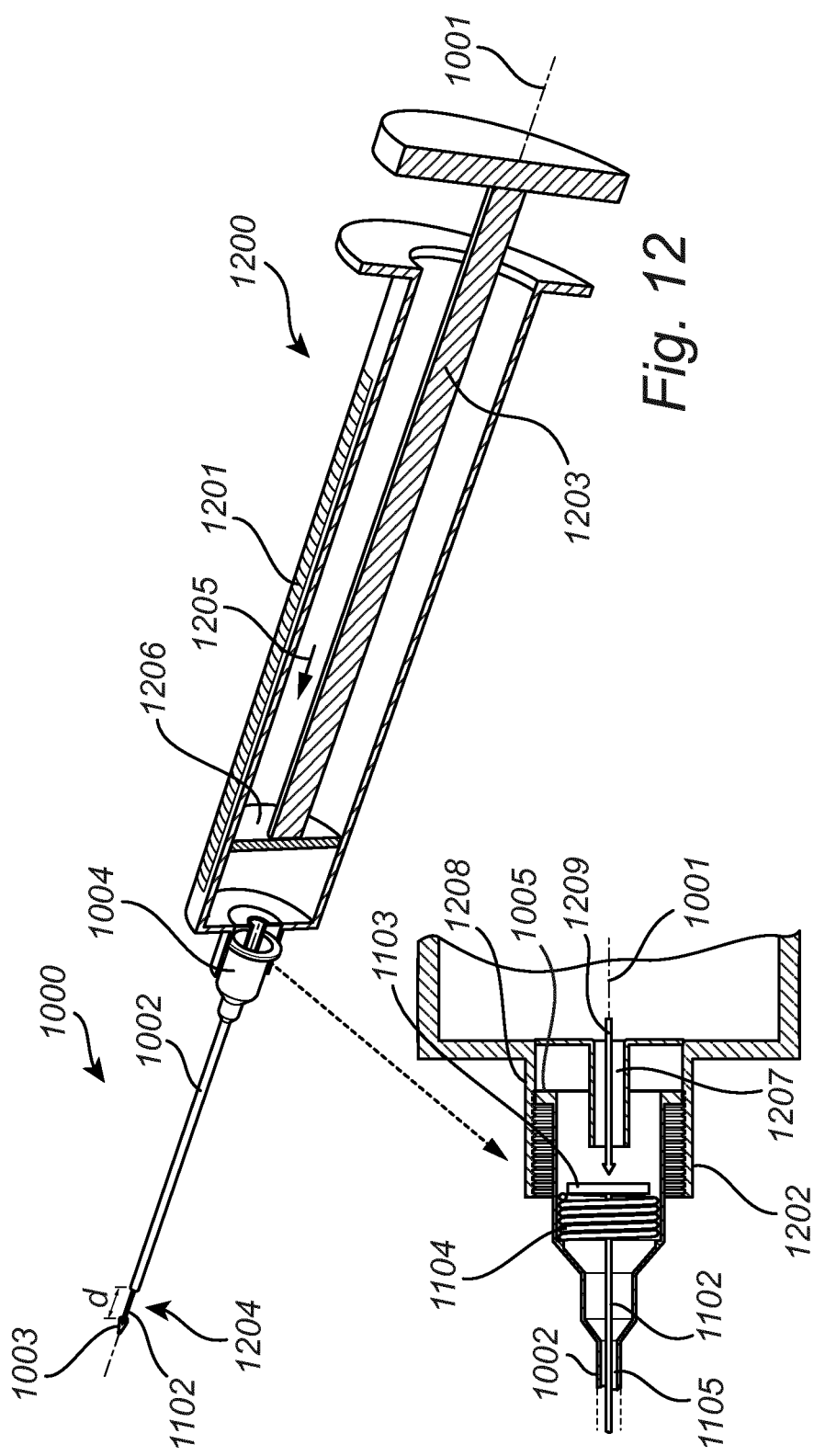
FIG. 12 illustrates a needle arrangement with a syringe connected thereto, and a close-up of a connection member of the needle arrangement.

An embodiment relating to an injection needle arrangement will be now be disclosed with reference to FIGS. 10-12.

Up to here, the geometry and function of various types of biopsy needle arrangements are presented and discussed. In the following, an embodiment relating to an injection needle arrangement will be disclosed.

FIG. 10 is a perspective view of an injection needle arrangement 1000 comprising a sealing member 1003, a needle sheath 1002, and a connection member 1004. An elongated portion (not shown in FIG. 10) of a needle is coaxially arranged inside the needle sheath 1002. The needle is movable relative to the needle sheath 1002 along a longitudinal axis 1001 of the needle. The needle sheath 1002 is arranged to sheath the elongated portion of the needle. The needle further comprises the sealing member 1003 which is arranged to a front end of the elongated portion of the needle.

The needle sheath 1002 has a front end and a rear end, and is arranged to cover the entire length of the elongated portion of the needle when the needle arrangement is set in a closed position, as in FIG. 10. By closed position is meant that the sealing member 1003 is arranged to abut at least a portion of a front end surface of the needle sheath 1002 extending transverse the longitudinal axis 1001 of the needle. As disclosed in previous embodiments, intrusion of foreign matter is thus restricted in an area between the needle sheath 1002 and the needle. As shown in FIG. 10, the rear end of the needle sheath 1002 is connected to the connection member 1004 which is adapted to connect to the tip of a syringe. The connection member 1004 comprises a circumferential flange 1005 arranged at a rear end of the connection member 1004. The connection member 1004 is by its front end arranged to the rear end of the needle sheath 1002.

The connection member 1004 will now be disclosed in detail with further reference to FIG. 11. FIG. 11 is a close-up perspective cross-sectional view of the connection member 1004 of the injection needle arrangement 1000 shown in FIG. 10. FIG. 11 illustrates a part of the needle 1102 arranged inside the needle sheath 1002. A channel 1105 is provided between the needle 1102 and the inner surface of the needle sheath 1002. The channel 1105 extends along the longitudinal axis 1001 of the needle 1102 between the front end to the rear end of the needle sheath 1002. The channel 1105 is formed by a gap between an outer surface of the needle 1102 and an inner surface of the needle sheath 1002.

It is advantageous to have a needle arrangement of any embodiment set and maintained in the closed position when the needle arrangement is not in an active mode, i.e. when it is not set in the open position for sampling (when taking a biopsy), for injection, or for aspiration. For this purpose, a biasing means may be provided. The biasing means may be arranged to bias the needle arrangement to be set in the closed position so as to ensure a tight sealing between the sealing member and the needle sheath.

Returning to FIG. 11, the connection member 1004 comprises such a biasing means in the form of a helical spring element 1104. The helical spring element 1104 extends parallel to the longitudinal axis 1001 between an inner wall portion 1106 of the connection member 1004 and an end plate 1103 being part of the needle 1102. That is, the helical spring element 1104 is arranged to be compressed in a direction extending at least partly along the longitudinal axis 1001. The compression axis may for example extend in parallel or be common with the longitudinal axis 1001. The end plate 1103 is arranged to, and connected to, a back portion of the needle 1102.

The dimensions and characteristics of the needle 1102, the connection member 1004, and the helical spring element 1106 is chosen such that the helical spring element 1106 is at least slightly compressed when arranged between the connection member 1004 and the end plate 1103. Thus, the helical spring element 1106 applies a force on the end plate 1103, and thus also on the rest of the needle 1102, in a backward direction. The sealing member 1003 (seen in FIG. 10) is thus forced backwards towards the needle sheath 1002, which in turn is forced in the opposite direction (forwards) by the helical spring element 1104. The helical spring element 1104 thus provides a biasing of the needle arrangement 1000 to be set in the closed position.

The injection needle arrangement 1000 may also be set in an open position, which is illustrated in FIG. 12. When the needle arrangement 1000 is set in the open position, a gap 1204 is formed between the sealing member 1003 and the front end surface of the needle sheath 1002. The gap 1204 is formed by that the relative position of the needle 1102 and the needle sheath 1002 is adjusted such that a front portion of the elongated portion of the needle 1102 is extracted from the needle sheath 1002.

In general, the adjustment may be achieved by moving the needle forward out from the needle sheath, or by moving the needle sheath backward to expose the needle, or by a combination of these adjustments. In the illustrated embodiment of the injection needle arrangement 1000, however, the adjustment is achieved mainly by a forward movement of the needle 1102 which will now be disclosed in detail.

In FIG. 12, a conventional syringe 1200 is connected to the connection member 1004 of the injection needle arrangement 1000. The syringe 1200 comprises a barrel 1201 formed by a hollow cylindrical tube and a plunger 1203 which can be pulled (for aspiration) or pushed (for injection) along the longitudinal axis 1001 of the needle 1102. An end plunger plate 1206 is attached to the front side of the plunger 1203 facing the needle arrangement 1000. The end plunger plate 1206 is arranged to provide a sealing against the barrel 1201.

The syringe 1200 is here of a conventional Luer lock type in which a tip 1202 of the syringe 1200 comprises an inner tip 1207 and an outer tip 1208. The inner surface of the outer tip 1208 is threaded for allowing the syringe 1200 to be screwed on a fitting such as the flange 1005 of the connection member 1004. In FIG. 12, the syringe 1200 is fitted on the connection member 1004 and the inner tip 1207 is located partly inside the connection member 1004. The connection member 1004 is arranged such that a sealed fitting is provided between the syringe 1200 and the connection member 1004.

The circumferential flange 1005 extends in a transverse direction to the longitudinal axis 1001. The circumferential flange 1005 may have a different cross-sectional shape than that of the rest of the connection member 1004. The injection needle arrangement 1000 shown in FIG. 10 comprises a connection member 1004 with a circumferential flange 1005 having a circular cross-sectional geometry but various other geometrical forms are possible. Non-limiting examples include rectangular and oval cross-sectional shapes. The circumferential flange, of any shape, may extend along the whole circumference a sub-portion thereof.

FIG. 12 illustrates the needle arrangement 1000 in an active mode, i.e. during injection by the syringe 1200. The plunger 1203 is pushed in a forward direction 1205, thus forcing a liquid located in the syringe in a forward direction 1209, along the longitudinal axis 1001, out from the syringe 1200 through the inner tip 1207 and into an inner space of the connection member 1004. The liquid exerts a pressure on the end plate 1103 of the needle 1102, which moves in a forward direction along the longitudinal axis 1001 whereby the helical spring element 1104 is compressed. The needle 1102 is thereby moved forwards in relation to the needle sheath 1002, thus exposing a front part of the elongated portion of the needle 1102. A longitudinal gap 1204 is formed which extends along the longitudinal axis 1001 of the needle 1102. The distance d between the sealing member 1003 and the needle sheath 1002, i.e. the length of the longitudinal gap 1204, may be 0.1-1 mm, but may be outside this range depending on embodiment.

When the needle arrangement 1000 is set in this open position, the liquid pushed out from the syringe 1200 is allowed to travel between the syringe 1200 and the gap 1204 through the channel 1105 provided between the needle 1102 and the needle sheath 1002. A fluid communication is thus allowed between the syringe 1200 and the gap 1204. At the front end of the needle sheath 1002, the channel 1105 is open towards a surrounding area to which the liquid may be injected. The injection needle arrangement 1000, with the syringe 1200 connected thereto, may be (at least partly) inserted into a tissue. When in place, the plunger 1203 is pushed thus setting the injection needle arrangement 1000 in the open position. The liquid of the syringe 1200 is thus injected into the tissue via the channel 1105. When the plunger 1203 is no longer pushed, or when reaching the front end of the barrel 1201, the liquid pressure will decrease whereby the forward force on the end plate 1103 also decreases. The helical spring element 1104 will thereby decompress from its compressed state and force the end plate 1103, and thus also the rest of the needle 1102, backwards. The injection needle arrangement 1000 is thereby set in the closed position and the needle arrangement 1000 may be retracted from the tissue in a sealed state providing a lowered risk of infection when compared to conventional injection needle arrangements.

The helical spring element 1104 is chosen such that the force required for compression corresponds to the force exerted by the liquid pressure in order to provide the above disclosed function of setting the needle arrangement 1000 in the open position. The configuration of the helical spring element 1104, or of an alternative biasing means, may of course vary between applications. The ability to design the needle arrangement 1000 in view of these characteristics is considered to be knowledge of the skilled person without the need for a more detailed explanation here.

It is appreciated that other types of biasing means may be used. Non-limiting examples include wave springs, spring mechanisms based on compression of air or gas, gas springs, volute springs, machined springs, and spring mechanism based on compression of an elastic material.

Moreover, the skilled person realizes that other types of syringes may be used and that the needle arrangement may be adapted for connection to those different types of syringes. For example, a slip tip syringe may be used which is fitted by a press fit. The connection is in in that case held together by friction between the syringe and a connection member of the needle arrangement.

In a needle arrangement, such as the one disclosed above, for an injection application, it is advantageous that the channel of the needle arrangement is provided between the needle and the needle sheath. In such a configuration, a flow of liquid may be present between the sealing member and a front end surface of the needle sheath. Specifically, when the liquid pressure decreases the sealing member will move towards and eventually abut the front end surface of the needle sheath. During this movement the liquid flow, i.e. flow of liquid from the syringe to the surroundings via the channel, also decreases but will be present throughout the movement. An advantage with the flow of liquid is that it counteracts that surrounding tissue is clamped between the sealing member and the front end surface of the needle sheath when the needle arrangement is set in the closed position. This advantage contributes to an optimal sealing. This is especially an advantage during procedures where multiple insertions with the same needle are performed in the tissue since a strong sealing may be kept throughout the procedure.

Figure 13A:
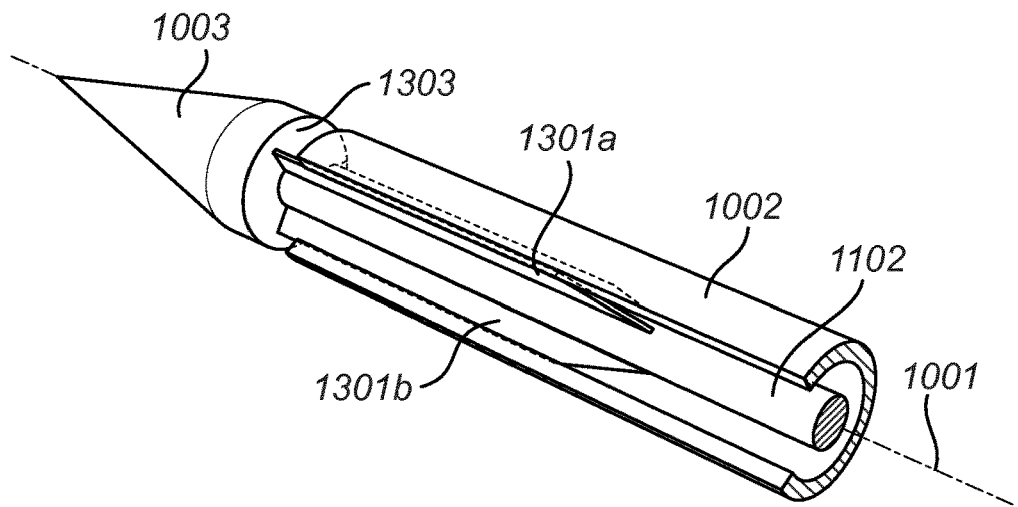
FIGS. 13a-13d illustrate different configurations of a part of a needle arrangement for providing a guiding mechanism.
Figure 13B:
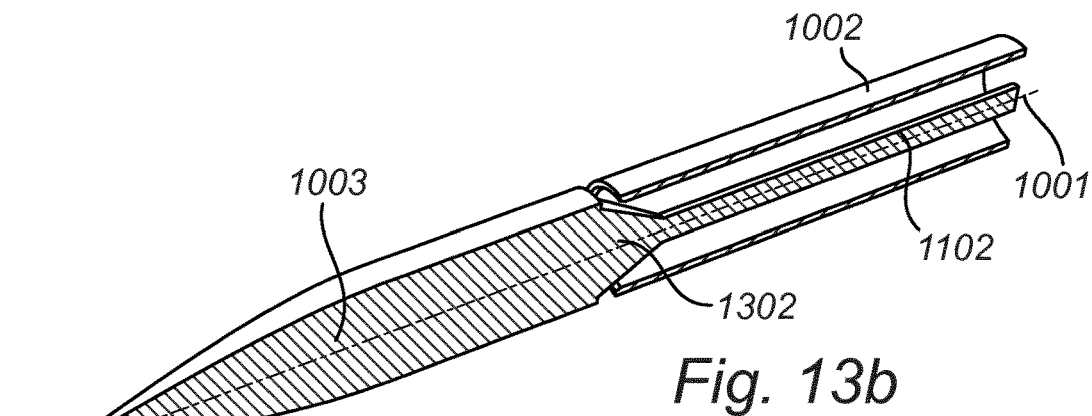

Different examples of a guiding portion for providing a guiding mechanism will now be disclosed with reference to FIGS. 13*a*-13*b*. It is appreciated that these configurations may be applied to needle arrangements of any embodiment, i.e. to a biopsy needle arrangement, to an injection needle arrangement, or to an aspiration needle arrangement.

FIGS. 13*a*-*b* is each a close-up perspective cross-sectional view of a front portion of a needle arrangement. The needle arrangement may be any one of the herein disclosed needle arrangement embodiments. The needle arrangement comprises a needle 1102 having a sealing member 1003 and an elongated portion. The elongated portion is adapted to be coaxially placed inside a needle sheath 1002 of the needle arrangement. These components have been disclosed in detail in connection to previously disclosed embodiments.

The needle 1102 further comprises, in each of the illustrated embodiments, one or more guiding portions for providing a guiding mechanism. The purpose of the guiding mechanism is to guide the sealing member 1003 towards an aligned position relative the needle sheath 1002 while the needle arrangement is set towards the closed position. By aligned position is meant a predetermined relative position between the sealing member 1003 and the needle sheath 1002 that is desired for an application. In a preferred embodiment where the sealing member 1003 is arranged to have the same cross-sectional shape and size as the needle sheath 1002 to provide a smooth transition between the outer surfaces of the sealing member 1003 and the needle sheath 1002, when the needle 1102 is arranged in the closed position. In such an embodiment, the aligned position may be the relative position between the sealing member 1003 and the needle sheath 1002 that provides the desired smooth transition. A smooth transition may contribute to a reduced risk of collecting bacteria in the needle arrangement.

Different examples of how the guiding portion may be formed will now be disclosed in detail.

In FIG. 13*a*, the guiding portion is formed by a plurality of flanges 1301*a*, 1301*b* that extend between the elongated portion of the needle 1102 and an inner wall of the needle sheath 1002. The flanges 1301*a*, 1301*b* may extend from a back end surface 1303 of the sealing member 1003 and along, for example, 1-3 mm of the elongated portion of the needle 1102. The flanges 1301*a*, 1301*b* preferably extend at least the length being the maximum length of the gap, between the sealing member 1003 and the front end of the needle sheath 1002, when the needle arrangement is set in the open position, in order to avoid any surrounding tissue to be caught by the back ends of the flanges 1301*a*, 1301*b*.

The plurality of flanges 1301*a*, 1301*b* may form an integral part of the needle 1102. Each of the flanges 1301*a*, 1301*b* may be formed with a decreasing width at a back end portion thereof. Thus, an inclined surface is provided for facilitating the guiding towards the aligned position.

In FIG. 13*b*, the guiding portion is formed by a conical portion 1302. The conical portion 1302 is formed around a longitudinal axis 1001 of the needle 1102. The conical portion 1302 is oriented with its base facing the sealing member 1003. In the illustrated embodiment, the conical portion 1302 is connected to the sealing member 1003. The conical shape of the conical portion 1302 facilitates the guiding towards the aligned position.

Figure 13C:
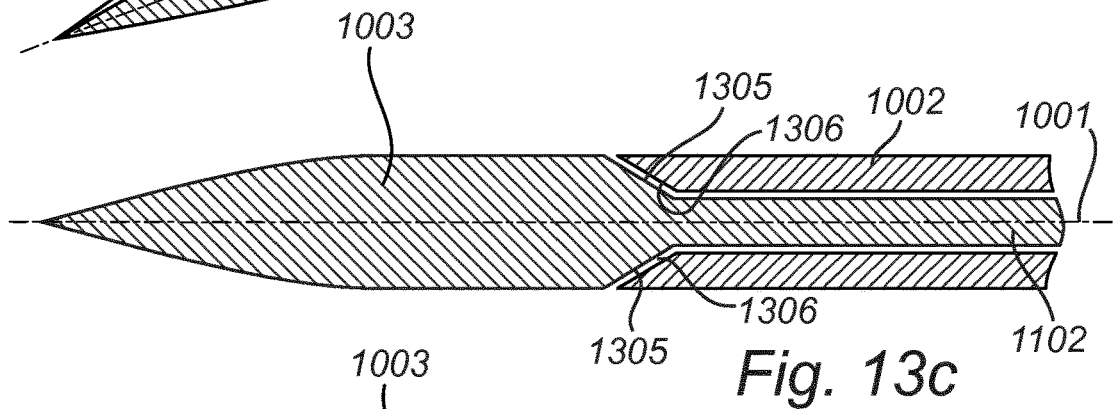
Figure 13D:
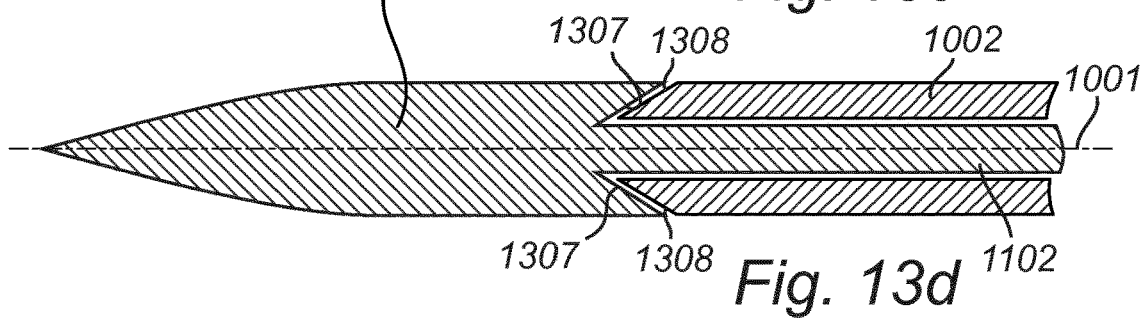

FIG. 13*c* and FIG. 13*d* illustrate alternative embodiments of a needle arrangement for providing the guiding mechanism. In these embodiments, the interface between the sealing member 1003 and the needle sheath 1002 is configured to provide the guiding mechanism.

In FIG. 13*c*, a back surface 1305 of the sealing member 1003 is inclined forwards in view of the longitudinal axis 1001 of the needle 1102. The front end surface 1306 of the needle sheath 1002 is inclined in a corresponding manner. A preferred inclination angle may be in the interval of 30-60 degrees relative the longitudinal axis 1001.

In FIG. 13*d*, a back surface 1307 of the sealing member 1003 is inclined backwards in view of the longitudinal axis 1001 of the needle 1102. The front end surface 1308 of the needle sheath 1306 is inclined in a corresponding manner. A preferred inclination angle may be in the interval of 30-60 degrees relative the longitudinal axis 1001.

Figure 14:
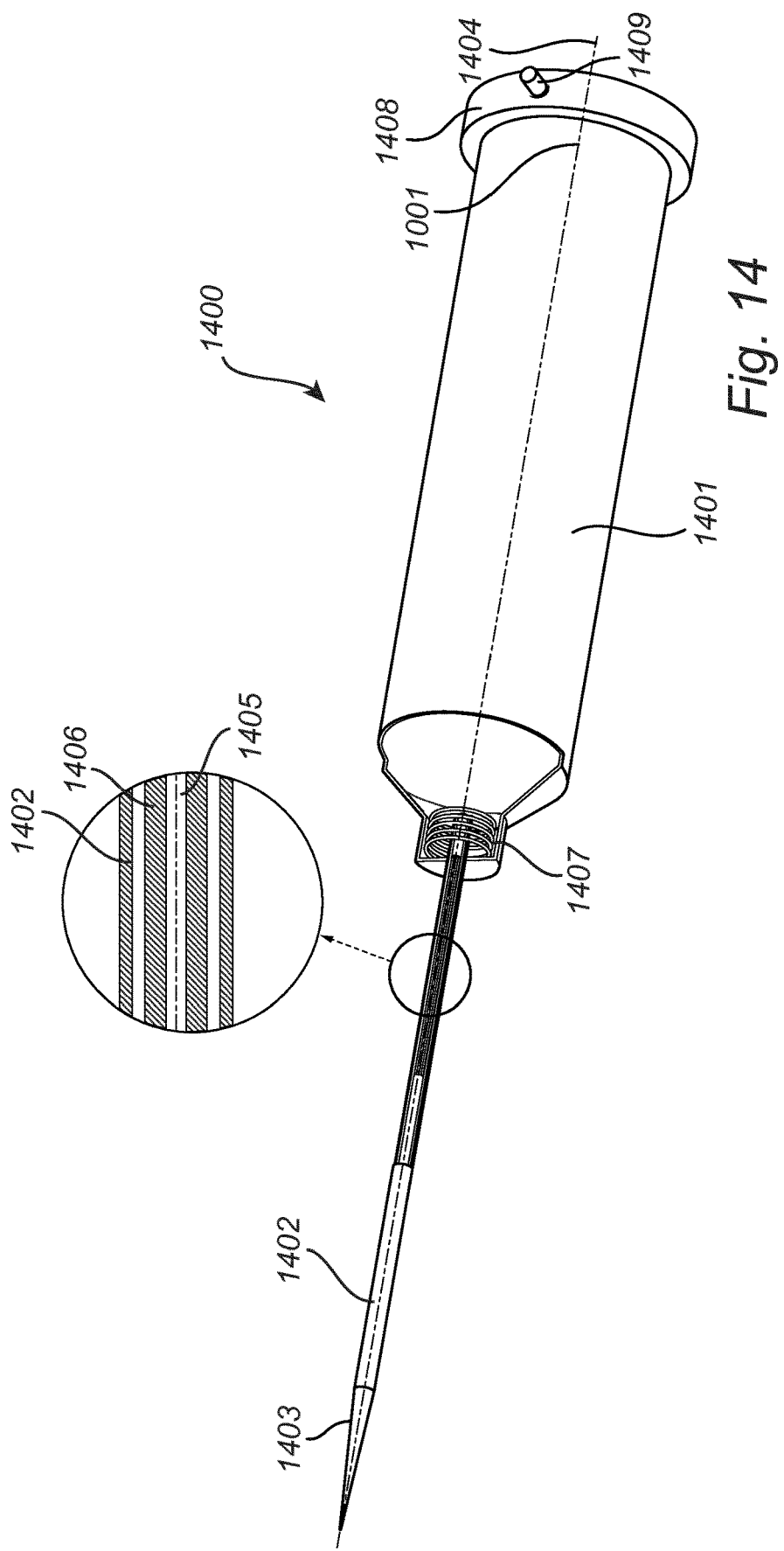
FIG. 14 illustrates a needle arrangement according to an embodiment of the invention.
Figure 15:
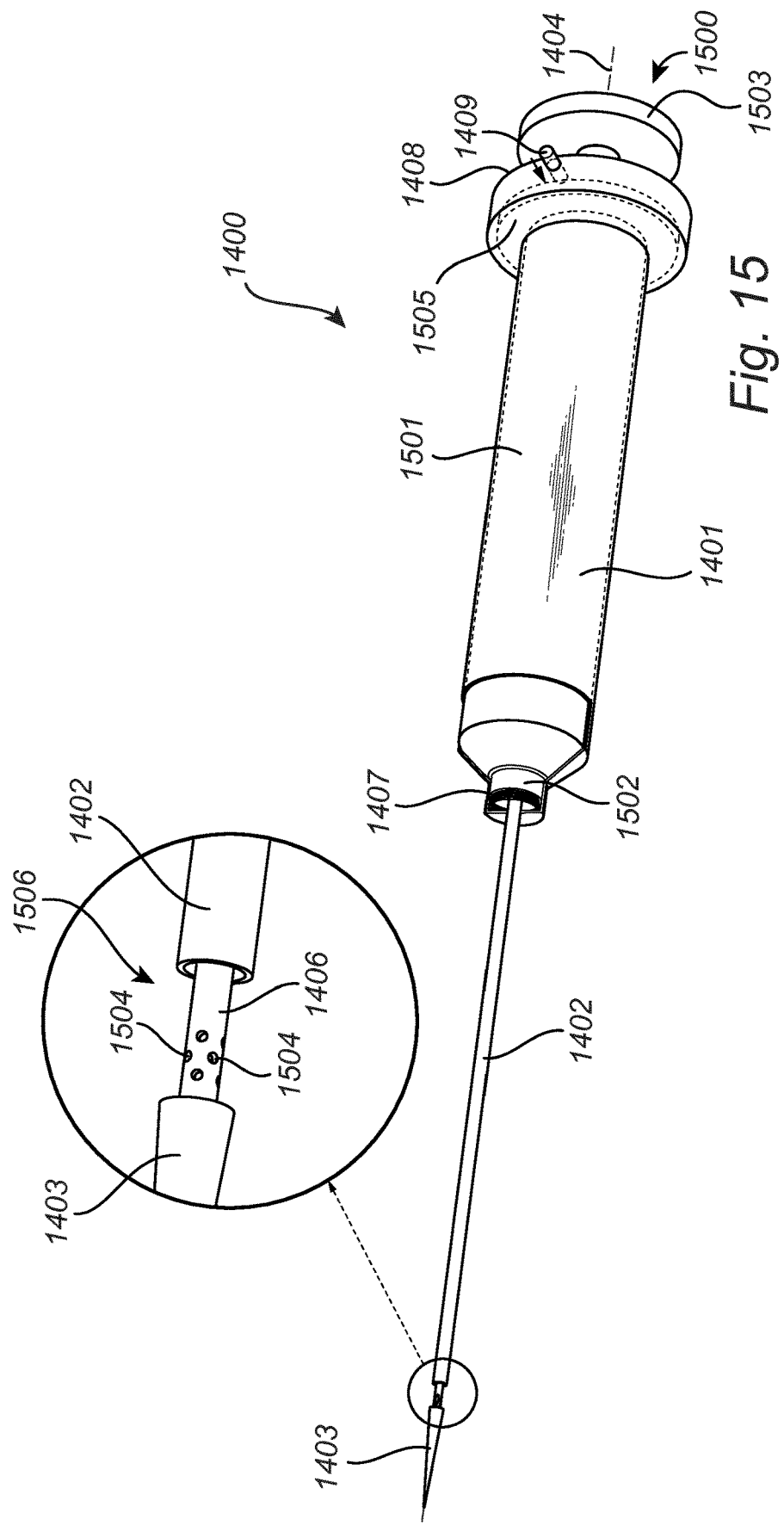
FIG. 15 illustrates the needle arrangement in FIG. 14 with a syringe inserted therein.

An embodiment relating to an aspiration needle arrangement will be now be disclosed with reference to FIGS. 14-15.

An aspiration needle arrangement 1400 is illustrated. As for the above disclosed needle arrangements, the aspiration needle arrangement 1400 comprises a needle sheath 1402 and a needle 1406. The needle 1406 comprises an elongated portion, adapted to be coaxially arranged inside the needle sheath 1402, and a sealing member 1403. The aspiration needle arrangement 1400 is arranged to be set in an open position and a closed position in the same manner as disclosed for above disclosed embodiments. In FIG. 14, the needle arrangement 1400 is set in the closed position. In FIG. 15, the needle arrangement 1400 is set in the open position.

The aspiration needle arrangement 1400 further comprises a connection member in the form of a syringe housing 1401 arranged at a rear end of the needle sheath 1402. The syringe housing 1401 is adapted to receive a syringe 1500, specifically (at least a part of) a barrel 1501 of the syringe 1500. It is appreciated that the syringe housing 1401 may have different forms for different applications. The syringe housing 1401 may preferably be made of a transparent material, such as a transparent plastic material, for allowing inspection of a syringe 1500 inserted therein during an aspiration process.

A channel 1405 is provided between a front end and the rear end of the needle sheath 1402. The channel 1405 extends along a longitudinal axis 1404 of the needle 1406. The channel 1405 is provided inside the needle 1406. In other embodiments of the aspiration needle arrangement, a channel may instead be provided between the needle 1406 and the needle sheath 1402.

The channel 1405 is provided for allowing a fluid communication between the syringe 1500 and a gap 1506 being formed when the needle arrangement 1400 is set in the open position, as illustrated in FIG. 15. The syringe housing 1401 is adapted to receive the syringe 1500 so as to allow a connection between a tip 1502 of the syringe 1500 to the needle 1406 for allowing a fluid connection therebetween. The needle 1406 may be provided with an appropriate connection configuration for enabling connecting of the tip 1502 thereto. Non-limiting examples of such connection configurations are a threaded connection and a slip tip configuration. These configurations are possible to achieve for the skilled person without the need for further details herein.

In order to allow a fluid connection between the channel 1405 and the surrounding area at a front end of the needle arrangement 1400, one or a plurality of apertures 1504 are provided in the elongated portion of the needle 1406. Each of the apertures 1504 connects the inner channel 1405 of the needle 1406 with the area outside the needle 1406. Hence, a fluid connection between the surrounding area at the front end of the needle arrangement 1400 and the syringe 1500 is provided, when the syringe 1500 is connected to the needle arrangement 1400 and to the needle 1406 thereof.

The syringe housing 1401 comprises a biasing means in the form of a helical spring element 1407. The biasing means is arranged to bias the needle arrangement 1400 to be set in the closed position. In this embodiment, the biasing towards the closed position is achieved when the syringe 1500 is received in the syringe housing 1401. The helical spring element 1407 extends at least partly along the longitudinal axis 1404 of the needle 1406, meaning that the helical spring element 1407 is arranged to be compressed in a direction extending at least partly along the longitudinal axis 1404. A compression axis of the helical spring element 1407 may for example extend in parallel or be common with the longitudinal axis 1404.

The helical spring element 1407 is located to extend between an inner wall of a front end of the syringe housing 1401 and an outer wall of a front portion of the barrel 1501 when the syringe 1500 is inserted into the syringe housing 1401, as illustrated in FIG. 15. Further, the needle 1406 is arranged such that, when the tip 1502 of the syringe 1500 is connected thereto, the needle 1406 may be forced along the longitudinal axis 1404 of the needle 1406 while the syringe 1500 is inserted into the syringe housing 1401. In other words, the length of the needle 1406 is chosen such as it is, when the syringe has been partly inserted into the syringe housing 1401 and connected to the needle 1406, moved forwards together with the syringe 1500 moving forwards. A front portion of the elongated portion of the needle 1406 is thus moved forwards in relation to the needle sheath 1402 whereby a longitudinal gap 1506 is provided between the sealing member 1403 and the needle sheath 1402. In other words, the injection needle 1400 is set from the closed position to the open position. In the open position, a fluid connection between the syringe 1500 and the area surrounding the front portion of the elongated portion of the needle 1406 is allowed. In the open position,
aspiration by the syringe 1500 is enabled by retraction of a plunger 1503 of the syringe 1500, thereby inducing a retraction force for aspirating a body liquid, such as blood, to the syringe 1500 via the apertures 1504 and the channel 1405.

It is appreciated that the apertures may be shaped and/or have a different size depending on embodiment. For example, for aspiration of viscous liquids, such as synovial fluid, the apertures may preferably be of a relatively large size.

As illustrated in FIG. 15, where the syringe 1500 is fully received in the syringe housing 1401, the helical spring element 1407 is arranged in a compressed mode. This configuration provides the function of a biasing towards the closed position of the needle arrangement 1400 since the syringe 1400 is forced backwards by the helical spring element 1407 when released. The needle 1406 is thereby also retracted into the needle sheath 1402 due to the connection between the needle 1406 and the syringe 1500. An advantage with this configuration is that a user does not need to manually retract the needle 1406 into the needle sheath 1402 for ensuring a sealing between the sealing member 1403 and the needle sheath 1402.

When compressed, the helical spring element 1407 thus applies a backward force on the inserted syringe 1500. A counteracting force needs to be applied to the syringe 1500 in order for it to stay inserted in the syringe housing 1401. For this purpose, a locking element may be provided. In the illustrated embodiment, the locking element comprises a locking pin 1409 that is arranged on a back end flange 1408 of the syringe housing 1401. The locking pin 1409 is arranged to be moved between an unlocking position and a locking position. While the syringe 1500 is inserted into the syringe housing 1401, the locking pin 1409 is set in an unlocking position. In FIG. 15, the locking pin 1409 that is illustrated in continuous lines is set in the unlocking position. When the syringe 1500 is fully inserted in the syringe housing 1401, the locking pin 1409 may be moved to the locking position by pushing the locking pin 1409 such that the locking pin 1409 is moved inwards (according to the arrow in FIG. 15) toward a longitudinal central axis of the syringe housing 1401. The locking pin 1409 may be movable between the unlocking position and the locking position with a similar mechanism as an ink cartridge is moved in a retractable pen, i.e. with a spring-loaded mechanism. In FIG.

15, the locking pin 1409 that is illustrated in broken lines is set in the locking position. In the locking position, the locking pin 1409 abuts the inserted syringe 1500 by abutting the plunger 1503. Thus, the locking pin 1409 counteracts the retracting force applied by the helical spring element 1407 on the syringe 1500. The needle arrangement 1400 is thereby lockingly set in the open position. An advantage by this configuration is that a user does not need to actively hold the syringe 1500 in the inserted position. This freedom provides for a less complex aspiration process.

It is appreciated that the locking mechanism provided by the locking element may be achieved in various other ways. For example, a locking mechanism similar to the mechanism of a retractable pen may be provided. In such an embodiment, the connecting member may comprise a spring-loaded mechanism which provides a lockingly setting of the needle arrangement in the open position when the syringe is inserted and pushed towards the spring mechanism. When performing a second pushing of the inserted syringe towards the spring mechanism and releasing, similar to a clicking of a button of a retractable pen, the spring mechanism is arranged to again bias the needle arrangement towards the closed position.

The skilled person realizes that the present invention by no means is limited to the preferred embodiments described above. On the contrary, many modifications and variations are possible within the scope of the appended claims.

For example, heating of the heat coating may be electrically induced through diathermy and the use of high-frequency electromagnetic waves, such as ultra sound, short-wave radio frequencies and microwaves.

The heating of the heat coating 702 may also be performed by focusing a laser on the coating, in which case the surrounding material, the needle 202 and/or the needle sheath 104 may be of a transparent material, such as a transparent plastic. The laser may be situated inside or outside the biopsy needle arrangement 100.

Variations to the disclosed embodiments can be understood and effected by the skilled person in practicing the claimed invention, from a study of the drawings, the disclosure, and the appended claims.

The invention claimed is:

1. A needle arrangement for a medical application, the needle arrangement comprising:
   an elongated needle sheath having a front end surface that is undivided and provided with an opening and a rear end, and
   a needle comprising:
      an elongated portion adapted to be coaxially arranged inside the needle sheath and extending through the opening, and
      a sealing member being arranged to a front end of the elongated portion,
      wherein the needle arrangement is adapted to be set in:
         a closed position, in which the sealing member and the needle sheath are forced towards each other, wherein the sealing member is arranged to abut the front end surface of the needle sheath, the front end surface extending transverse to a longitudinal axis of the needle thereby restricting intrusion of foreign matter in an area between the needle sheath and the needle, and
         an open position, in which a gap, extending in the longitudinal axis of the needle, is formed between the sealing member and the front end surface of the needle sheath.

2. The needle arrangement according to claim 1, further comprising:
   a connection member positioned at the rear end of the needle sheath and adapted to connect to an actuator or to a syringe.

3. The needle arrangement according to claim 2, wherein the connection member comprises a biasing member arranged to cooperate with the needle arrangement and bias the needle arrangement to be set in the closed position.

4. The needle arrangement according to claim 3,
   wherein a channel is provided between the front end surface and the rear end of the needle sheath, said channel extending along the longitudinal axis (1001, 1404) of the needle,
   wherein the channel is provided between the needle sheath and the needle or inside the needle, and
   wherein the syringe is connectable to the needle arrangement by means of the connection member providing a fluid communication between the syringe and the gap through the channel when the needle arrangement is set in the open position.

5. The needle arrangement according to claim 4, wherein the connection member is arranged to connect to a tip of the syringe.

6. The needle arrangement according to claim 5,
   wherein the channel is provided between the needle sheath and the needle.

7. The needle arrangement according to claim 6,
   wherein the biasing member comprises a spring member extending in parallel to the longitudinal axis of the needle and between the connection member and a part of the needle,
   wherein the spring member is arranged to be compressed in response to a liquid pressure during injection of a liquid by the syringe, wherein the needle arrangement is arranged to be set in the open position in response to the compression of the spring member.

8. The needle arrangement according to claim 7,
   wherein the spring member comprises a spring element extending between an inner wall portion of the connection member and an end plate arranged to a back portion of the needle.

9. The needle arrangement according to claim 6,
   wherein the needle comprises a guiding portion arranged to a front portion of the elongated portion for guiding the sealing member towards an aligned position relative the needle sheath while the needle arrangement is set from the open position to the closed position.

10. The needle arrangement according to claim 9, wherein the guiding portion comprises a plurality of flanges extending between the elongated portion of the needle and the needle sheath.

11. The needle arrangement according to claim 9, wherein the guiding portion comprises a conical portion having a base, wherein the conical portion is formed around the longitudinal axis of the needle and oriented with the base facing the sealing member.

12. The needle arrangement according to claim 4,
   wherein the channel is provided inside the needle,
   wherein a rear end of the needle is arranged to connect to a tip of the syringe,
   wherein the connection member comprises a syringe housing adapted to receive at least a part of a barrel of the syringe, and
   wherein the needle is forced forward along a longitudinal axis in response to the tip of the syringe connecting with the rear end of the needle thereby setting the needle arrangement in the open position.

13. The needle arrangement according to claim 12, wherein the biasing member comprises a spring extending in parallel with the longitudinal axis of the needle and arranged to extend between the connection member and a front portion of the barrel of the syringe when received in the syringe housing.

14. The needle arrangement according to claim 12, wherein the connection member comprises a lock for locking the barrel of the syringe when received in the syringe housing for lockingly setting of the needle arrangement in the open position.

15. The needle arrangement according to claim 2, wherein a compartment is provided in the elongated portion of the needle such that the compartment is exposed to a surrounding area when the needle arrangement is set in the open position.

16. The needle arrangement according to claim 1, wherein a heat coating is provided on at least a distal outer surface of the sealing member, wherein
   the coating is arranged to be heated up by providing a current through the heat coating, or
   the coating is arranged to be heated up by radiation provided by an external energy source, or
   the heat coating is arranged to be heated by subjecting it to radiation from an external energy source.

17. The needle arrangement according to claim 1, wherein the sealing member and the needle sheath have a same cross-sectional shape and size.

\* \* \* \* \*

UNITED STATES PATENT AND TRADEMARK OFFICE
CERTIFICATE OF CORRECTION

PATENT NO.        : 11,701,474 B2
APPLICATION NO.   : 16/324548
DATED             : July 18, 2023
INVENTOR(S)       : Andreas Forsvall Page 1 of 1

It is certified that error appears in the above-identified patent and that said Letters Patent is hereby corrected as shown below:

On the Title Page

Item (73) should read as follows:
XAGA SURGICAL AB          HELSINGBORG, (SE)

Signed and Sealed this
Twenty-third Day of July, 2024

*Katherine Kelly Vidal*

Katherine Kelly Vidal
*Director of the United States Patent and Trademark Office*